(12) United States Patent
Yoshinaga et al.

(10) Patent No.: US 11,877,996 B1
(45) Date of Patent: Jan. 23, 2024

(54) ARSINOTHRICIN AS A MULTI-STAGE ANTIMALARIAL

(71) Applicants: Masafumi Yoshinaga, Doral, FL (US); Barry P. Rosen, Boynton Beach, FL (US); Jun Li, Miami, FL (US); Guodong Niu, Miami, FL (US)

(72) Inventors: Masafumi Yoshinaga, Doral, FL (US); Barry P. Rosen, Boynton Beach, FL (US); Jun Li, Miami, FL (US); Guodong Niu, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 18/219,903

(22) Filed: Jul. 10, 2023

(51) Int. Cl.
*A61K 31/285* (2006.01)
*A61P 33/06* (2006.01)

(52) U.S. Cl.
CPC ............ *A61K 31/285* (2013.01); *A61P 33/06* (2018.01)

(58) Field of Classification Search
CPC ....... A61B 17/083; A61B 17/10; A61B 17/29; A61K 2300/00; A61K 31/285; A61K 45/06; A61P 31/04; C07F 9/72; C12P 13/001; C12P 13/04; C12P 9/00; C12Y 201/01137; C12Y 203/01183
See application file for complete search history.

(56) References Cited

U.S. PATENT DOCUMENTS

| | | |
|---|---|---|
| 11,298,335 B2 | 4/2022 | Rosen et al. |
| 11,396,520 B2 | 7/2022 | Rosen et al. |
| 2020/0121632 A1 * | 4/2020 | Rosen .................. A61K 31/285 |

OTHER PUBLICATIONS

Howlader, Hasan A. et al. "Chemical synthesis of the organoarsenical antibiotic arsinothricin." RSC Adv., 11 (56):35600-35606, (Year: 2021).
Nadar, Venkadesh Sarkarai et al. "Arsinothricin, an arsenic-containing non-proteinogenic amino acid analog of glutamate, is a broad spectrum antibiotic." Communications Biology, 2(131):1-12, (Year: 2019).
Suzol, Sazzad H. "Semisynthesis of the Organoarsenical Antibiotic Arsinothricin." J Nat Prod. 83(9):2809-2813, (Year: 2020).
Yoshinaga, Masafumi et al. "Arsinothricin Inhibits Plasmodium falciparum Proliferation in Blood and Blocks Parasite Transmission to Mosquitoes." Microorganisms, 11(5):1195, May 3, 2023.

* cited by examiner

*Primary Examiner* — Savitha M Rao
(74) *Attorney, Agent, or Firm* — SALIWANCHIK, LLOYD & EISENSCHENK

(57) ABSTRACT

The subject invention provides arsinothricin (AST) or salts thereof, and compositions comprising AST or a salt thereof for use as multi-stage antimalarials. The subject invention also provides methods for treating, inhibiting and/or preventing malaria infection and transmission by using AST or salts thereof, or compositions comprising AST or a salt thereof. Advantageously, AST or a salt thereof inhibits glutamine synthetase (GS) of malaria pathogens without exhibiting cytotoxicity to human host.

20 Claims, 11 Drawing Sheets
Specification includes a Sequence Listing.

| | | |
|---|---|---|
| P.falciparum | MLIKLFFSNMAELYEYIKD-----RKMDVEIVACIITNLLGTYFKCFFYVKEITLNK--L | 53 |
| E.coli | -------MSAE-NVLTML-------NEHEVKFVDLRFTDTKEKEQHVTIPAHQVNAKF--F | 44 |
| H.sapiens | ----MTTSASSHLNKGIKQVYMSLPQGEKVQAMYIWIDGTGEGLRCKTRTLDSEPKCVEE | 56 |
| | *  ,  . :  :   :   ,   :  *   *   ,   :   ( | |
| P.falciparum | ESGFSPEASEIKLCSDTEVSDFFIKVDHSTCYLECDGKNILNIMCDIKRYNGP-DYYKC | 112 |
| E.coli | EEGRMFEGSEIGGWKGINESDNVLMPDASTAVIDPFFADSTLIIRCDILEPGTLQGYDRD | 104 |
| H.sapiens | LPEWNFEGSETLQSE-GSNSDMILVPA--ANFRDPFRKDPNKLVLCEVFKINRRP----- | 109 |
| | , .     .  ** :       :    .  *::  , . | |
| P.falciparum | FRTILKKTCEFVRNEGIADRVCIGKELEFFIFDKVNISLDEYNTTLKVIDRESPSCKNDL | 172 |
| E.coli | FASIAKNAEDYLASYGIADTYLFGKEFFLFDDIRFGSSIAGSHVAIDDIE--------- | 156 |
| H.sapiens | AKTNLRHTCKRIMDMVSNQHPWFGEKETTLMGTDGH----------------------- | 145 |
| | :  :  (:)  . , .        :* . .  )) . | |
| P.falciparum | SSIYGHHYVNKVEFHKDHFNNPNNEYLIHDDSKRVKRRSGEFTDFYDTS--NI---IKL | 227 |
| E.coli | -G---------------A-WNSBTQYEGKSNKGHRFAVRSGEFFVPPVDSA--QD---IRS | 194 |
| H.sapiens | --------------PFGWPSNGFPG----------PQGPETCGVGADRAYGRDIVEARY | 180 |
| | .:  (()   ,   *   . : | |
| P.falciparum | RICRALNDMNINVQRYNHEVSTS-QHEISLRYFDALTRADFLLITRQIINTTVSSFNRIA | 286 |
| E.coli | EMCLVMEQMGLVVEAHHHEVATAGQKEVATRFNTMTKRADEIQIYRYVVHNVAHRFGRTA | 254 |
| H.sapiens | RACLY---AGVKIAGTRAENKPA-QKEFQIGFCKGISMEDHLNVARFILMRVCKDFGVIA | 236 |
| | . *    .    .   .:**  * .*   .* ( ((  :):  , * . * | |
| P.falciparum | TFMFKFLVHD-EENGLECHIELWKNNKNIFYHNDFST---FFLSKESPYFMTGIVKHAKAL | 343 |
| E.coli | TFMFKMFGD-ESGMECHMELSKNGVNLFAGDRY-----AGLSEQALYYIGGVIKHAKAY | 309 |
| H.sapiens | TFDFKPIFGNWEAGCEIKFG--TKAMREKNGLKYIEKAISKLSKRHQYHI--------- | 285 |
| | ** *** ;   ::   **  *  .*   *  .             **(.   *(: | |
| P.falciparum | QAFC-NATMNSYKELVPGFETCQK--LFYSPGSESAVIELSLINYSNPSERRIEELPDC | 400 |
| E.coli | NALA-NPTTNSYKELVPGYEAPVM--LAYSARNECASIEIPVV--SSPKARRIEEFPDP | 364 |
| H.sapiens | RAYDPKGGLDNAREILTGFHETSNINDPSAGVAXECASIEIPRTVG-QEKKGYFEEBFSA | 344 |
| | .*  : (.  .;*. .*    .   .  :*** **:           ..  *: | |
| P.falciparum | ANSPHLVMAAIILAGYDGIKSKEQPLVPFFSKDNHFYISSIFSKYVQHPENFNILTHALE | 460 |
| E.coli | AANPYLCFAALLMAGLDGIKNWRIHPGEAMDK---NLYD---------LPFEE----- | 404 |
| H.sapiens | NCDPFFSVTEALIRTCLLNE-----TGDEFFQYKN------------------- | 373 |
| | .*.  *::  (  .           (( | |
| P.falciparum | GYESLMTINESPEFKNFFKCEEPQGISPELVESLDALEKDHAPLTVNNIFTKEMIQEYIK | 520 |
| E.coli | --------------AKEIPQVAGSLEEALNELDLDREFLKAGGVFTDEAIDAYIA | 445 |
| H.sapiens | ----------------------------------------------- | 373 |
| P.falciparum | FKREEIDAYNKIVNAIDYHLYYEC | 544 |
| E.coli | LREKEDDRVENTFHFVKFELYYSV | 469 |
| H.sapiens | ------------------------ | 373 |

FIG. 8

ARSINOTHRICIN AS A MULTI-STAGE ANTIMALARIAL

GOVERNMENT SUPPORT

This invention was made with government support under AI125657 and GM136211 awarded by the National Institutes of Health. The government has certain rights in the invention.

SEQUENCE LISTING

The Sequence Listing for this application is labeled "SeqList-06Jul23.xml," which was created on Jul. 6, 2023, and is 4,653 bytes. The entire content is incorporated herein by reference in its entirety.

BACKGROUND OF THE INVENTION

Malaria is one of the most severe vector-borne diseases. It is estimated to have caused 241 million new cases and 627,000 deaths in 2020 worldwide. Human malaria is caused by five different *Plasmodium* species and transmitted by several *Anopheles* species. Among these species, *P. falciparum* and *P. vivax* are responsible for 99% of malaria cases.

*Plasmodium* species have a complex life cycle composed of specialized developmental forms in the mosquito vector and human host, i.e., sexual form in *Anopheles* mosquitoes and asexual form in humans. Unlike most other diseases, *Plasmodium* development in Anopheline mosquitoes is essential for malaria transmission. When a mosquito takes blood from a malaria patient, haploid microgametes and macrogametes form diploid zygotes that transform into mobile ookinetes. Mobile ookinetes will overcome the physical barrier of the mosquito midgut including peritrophic matrix (PM) and endothelium sequentially to initiate the infection in mosquitoes.

Even though a malaria vaccine (RTS,S/AS01) has recently been recommended by the World Health Organization (WHO), vector control is still one of the major methods against mosquito-transmitted diseases. Since the passage of *Plasmodium* through vector mosquitoes is a necessary step for malaria transmission, using insecticides to control the mosquito population has traditionally been an effective method to prevent the disease. Vector control relies heavily upon chemical insecticides against adult mosquitoes, mostly pyrethrin and its synthetic derivatives, pyrethroids.

Because no new classes of insecticides have been put onto the market in nearly 30 years, multiple primary mosquito vectors have developed resistance to pyrethroid insecticides. In addition, the rapid spread of resistant parasites to the frontline antimalarials (e.g., artemisinin) emphasizes the need for new antimalarials. Also, most antimalarials target only the symptomatic asexual blood stage. Thus, to ensure malaria elimination and eradication, new drugs with novel mechanisms of action and efficacy on multiple stages are highly desired.

BRIEF SUMMARY OF THE INVENTION

The subject invention provides agents/compounds, and compositions for use as antimalarials, and methods for treating and preventing malaria infection and transmission. Advantageously, the subject antimalarial agents/compounds, and compositions can be used to inhibit, for example, the essential enzyme glutamine synthetase (GS) of malaria pathogens with less toxicity to the human host.

The subject invention relates to the use of arsinothricin (2-amino-4-(hydroxymethylarsinoyl)butanoate or AST) or a salt thereof as a potent multi-stage antimalarial. AST is a potent inhibitor of *Plasmodium* glutamine synthetase (PfGS-I), and can be used as a multistage antimalarial. AST prevents growth of *P. falciparum* in the blood stage and transmission to mosquitoes. AST is both permeable and stable, and exhibits low toxicity in several human cell lines. Thus, AST selectively inhibits transmission of malaria pathogens and is relatively benign to the human host.

In one embodiment, the antimalarial agents/compounds and compositions comprising the antimalarial agent/compound can be used to treat, inhibit and/or prevent malaria infection and/or transmission to mosquitos. In specific embodiments, the antimalarial agent/compound is selected from AST and salts thereof.

In one embodiment, the subject invention provides a method of treating, inhibiting or preventing malaria infection in a subject in need thereof, the method comprising administering the antimalarial agent/compound or the composition of the subject invention to the subject in an amount effective to treat, inhibit, or prevent malaria infection in the subject.

Also provided is a method of inhibiting, reducing or preventing malaria transmission to mosquitoes, the method comprising administering the antimalarial agent/compound or the composition of the subject invention to the subject in an amount effective to inhibit, reduce or prevent malaria transmission.

In one embodiment, the subject invention provides a method of treating malaria infection in a subject in need thereof comprising administering to the subject AST or a salt thereof.

In one embodiment, the subject invention provides a method of inhibiting or reducing malaria transmission, the method comprising administering to a subject AST or a salt thereof, preferably, the subject being a human having been infected by a malaria parasite.

In one embodiment, the subject invention provides a method of inhibiting or reducing the growth of malaria parasite in a subject, the method comprising administering to the subject AST or a salt thereof.

In specific embodiments, malaria is caused by *P. falciparum, P. malariae, P. ovale, P. vivax, P. knowlesi, P. berghei, P. chabaudi* or *P. yoelii*.

In a specific embodiment, the AST is D-AST, L-AST or a combination thereof.

In certain embodiments, the administration is via oral, pulmonary, buccal, suppository, intravenous, intraperitoneal, intranasal, intramuscular, or subcutaneous route.

In certain embodiments, the salt of AST is: i) with an acid selected from hydrochloric acid, hydrobromic acid, perchloric acid, nitric acid, thiocyanic acid, sulfuric acid, phosphoric acid, trifluoroacetic acid (TFA), formic acid, acetic acid, propionic acid, lactic acid, pyruvic acid, oxalic acid, malonic acid, succinic acid, maleic acid, and fumaric acid, hexanoic acid, cyclopentanepropionic acid, glycolic acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-di sulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid; ii) with a base selected from sodium hydroxide, ammonium hydroxide, potassium hydroxide, monoalkyl amine, dialkyl amine, trialkyl amine, aryl amine, ammonium, and tetraalkylammonium; or iii) with a metal selected from sodium, potassium, calcium, and magnesium.

In some embodiments, the method further comprises detecting the activity of glutamine synthetase of the malaria parasite.

BRIEF DESCRIPTION OF THE DRAWINGS

FIG. 8 shows multiple protein sequence alignment of PfGS-I (SEQ ID NO: 1), E. coli GS-I (EcGS-I) (SEQ ID NO: 2) and hGS-II (SEQ ID NO: 3). Residues involved in the binding of glutamate (upward arrows), ATP (downward arrows), and ammonia (diamonds) are highlighted. Residues predicted to be involved in the binding of AST are highlighted by inverted triangles. Asterisks indicate fully conserved residues. Colons and periods indicate conservations between groups of strongly and weakly similar properties, respectively.

BRIEF DESCRIPTION OF THE SEQUENCES

Figure 1:
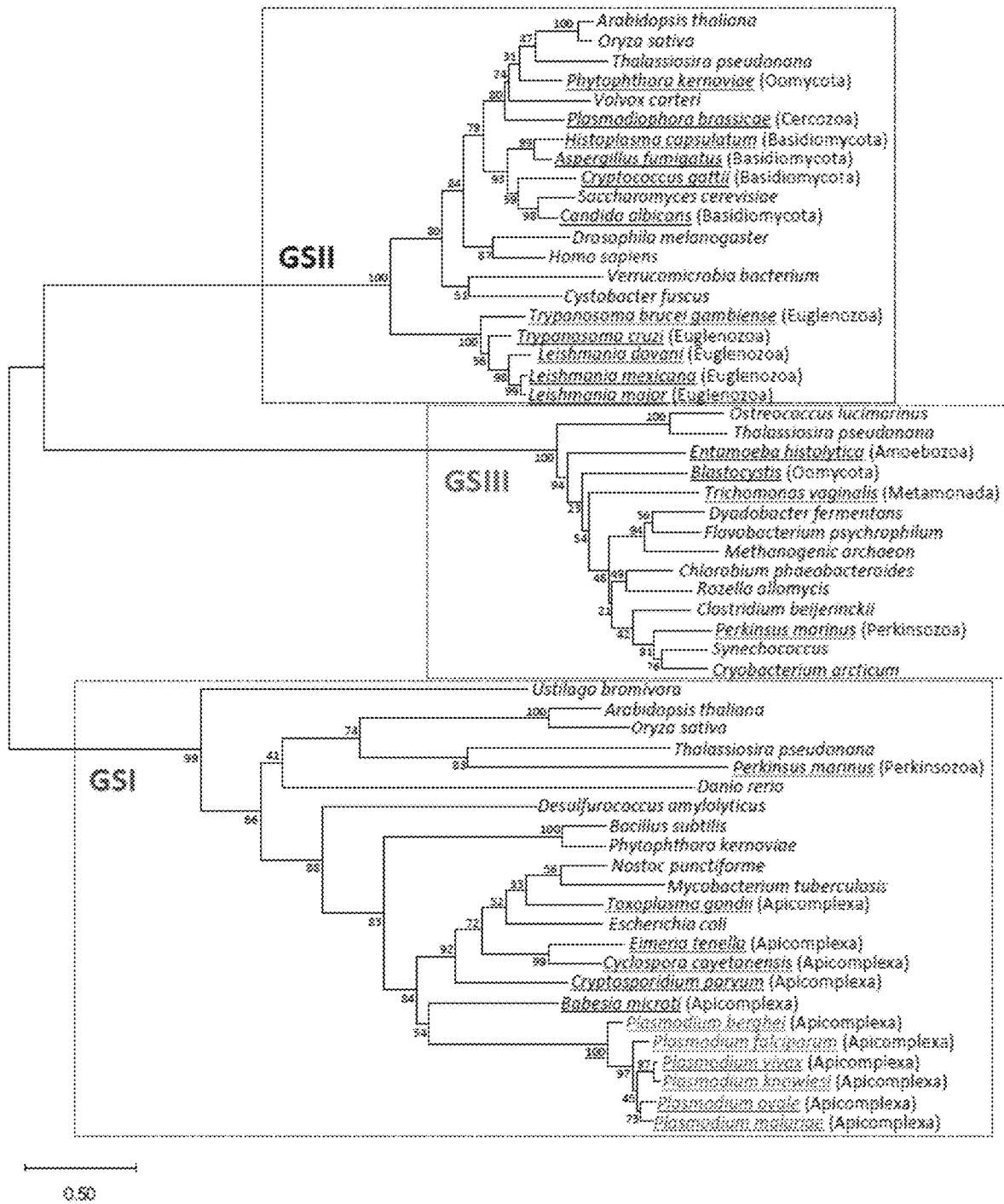
FIG. 1 shows phylogenetic tree of glutamine synthetases. The neighbor-joining phylogenetic tree shows the evolutionary relationships of glutamine synthetase orthologs from representative members of the three distinct groups GS-I, GS-II, and GS-III. GSs from parasites are underlined and their phyla or divisions are given in parentheses. Plasmodium species and Homo sapiens are highlighted in gray. Bootstrap values calculated for 1000 subsets (%) are indicated on each branch. NCBI accession numbers of proteins are given in Materials and Methods. The scale bar represents 50% sequence dissimilarity.

SEQ ID NO: 1 is an amino acid sequence of PfGS-I contemplated for use according to the subject invention.

SEQ ID NO: 2 is an amino acid sequence of EcGS-I contemplated for use according to the subject invention.

SEQ ID NO: 3 is an amino acid sequence of hGS-II contemplated for use according to the subject invention.

DETAILED DESCRIPTION OF THE INVENTION

The subject invention provides agents/compounds, and compositions for use as antimalarials, and methods for treating and preventing malaria infection and transmission. Advantageously, the subject antimalarial agents/compounds, and compositions can be used to inhibit, for example, GS of malaria parasites with exhibiting less toxicity to the human host. In one embodiment, the subject invention provides an antimalarial agent selected from arsinothricin (2-amino-4-(hydroxymethylarsinoyl)butanoate or AST) and salts thereof.

This disclosure shows that AST (FIG. 4B) is a potent inhibitor of *Plasmodium* GS (PfGS-I), and can be used as a multistage antimalarial by targeting PfGS-I. The parasite enzyme, PfGS-I, is phylogenetically closer to prokaryotic GS, or type-I GS (GS-I), than to eukaryotic GS, or type-II GS (GS-II). This disclosure demonstrates that AST prevents growth of *P. falciparum* in the blood stage and transmission to mosquitoes. In several human cell lines, AST is both permeable and stable, and exhibits low toxicity. Thus, AST selectively inhibits malaria pathogens and is relatively benign to the human host. Surprisingly, the permeability of AST in human erythrocytes is low, suggesting that AST reduces parasitemia by attacking merozoites released from schizonts rather than inhibiting proliferation of intracellular parasites.

AST, an arsenic-containing natural product produced by the rice rhizosphere bacterium *Burkholderia* sp. GSRB05, is a nonproteinogenic amino acid analog of glutamic acid that irreversibly inhibits bacterial GS. AST is an arsenic mimetic of phosphinothricin (PT) (FIG. 4B) and methionine sulfoximine (MSO) (FIG. 4B), which are natural products that inhibhit GS. AST is effective against various pathogens, while exhibits low cytotoxic to multiple human cell lines, demonstrating the ability to address the global threat of drug resistance.

Antimalarial Compositions

In one embodiment, the subject invention provides a therapeutic or pharmaceutical composition comprising a therapeutically effective amount of the antimalarial agents/compounds of the subject invention and a pharmaceutically acceptable carrier.

In specific embodiments, the therapeutic or pharmaceutical composition comprises AST or a salt thereof. Pharmaceutically acceptable salt as used herein includes, for example, salts that have the desired pharmacological activity of the parent compound (salts which retain the biological effectiveness and/or properties of the parent compound and which are not biologically and/or otherwise undesirable).

In specific embodiments, the AST is D-AST, L-AST or a combination thereof.

In one embodiment, the antimalarial agents/compounds and/or the composition comprising the antimalarial agents/compounds can stop malaria transmission to mosquitoes, inhibit malaria infection and inhibit parasite proliferation.

In some embodiments, the therapeutic or pharmaceutical composition further comprises one or more therapeutic agents for malaria including, for example, atovaquone-proguanil (Malarone), quinine sulfate (Qualaquin), doxycycline, Primaquine phosphate, chloroquine, mefloquine, and tafenoquine.

In one embodiment, the antimalarial agents/compounds, and compositions of the subject invention can be administered to the subject being treated by standard routes, including oral, inhalation, or parenteral administration including intravenous, subcutaneous, topical, transdermal, intradermal, transmucosal, intraperitoneal, intramuscular, intracapsular, intraorbital, intracardiac, transtracheal, subcutaneous, subcuticular, intraarticular, subcapsular, subarachnoid, intraspinal, epidural and intrasternal injection, infusion, and electroporation.

In one embodiment, the composition is formulated in accordance with routine procedures as a pharmaceutical composition adapted for local administration to a subject, e.g., humans. Typically, compositions for local administration are solutions in a sterile isotonic aqueous buffer. Generally, the ingredients are supplied either separately or mixed together in unit dosage form, for example, as a dry lyophilized powder or water free concentrate in a hermetically sealed container such as an ampoule or sachette indicating the quantity of active agent.

In one embodiment, the antimalarial agents/compounds and the pharmaceutical composition of the subject invention may be formulated in the forms of powders, dressings, creams, ointments, solutions, micellar solutions, emulsions, microemulsions, pastes, suspensions, gels, foams, oils, aerosols, granules, solids, or sprays.

In some embodiments, the compounds may be in the foam of a solvate. Solvates contain either stoichiometric or non-stoichiometric amounts of a solvent in physical association the compound or salt thereof. The solvent may be, for example, and without limitation, a pharmaceutically acceptable solvent. For example, hydrates are formed when the solvent is water or alcoholates are formed when the solvent is an alcohol.

The pharmaceutical dosage forms suitable for injection or infusion can include sterile aqueous solutions or dispersions or sterile powders comprising AST or a salt thereof that are adapted for the extemporaneous preparation of sterile injectable or infusible solutions or dispersions, optionally encapsulated in liposomes. Preferably, the ultimate dosage form should be sterile, fluid, and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof.

The proper fluidity can be maintained by, for example, the formation of liposomes, by the maintenance of the required particle size in the case of dispersions, or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by the use in the compositions of agents delaying absorption, for example, aluminum monostearate and gelatin.

Sterile injectable solutions are prepared by incorporating AST or a salt thereof in the required amount in the appropriate solvent as described herein with various of the other ingredients enumerated herein, as required, preferably followed by filter sterilization. In the case of sterile powders for the preparation of sterile injectable solutions, the preferred methods of preparation are vacuum drying and freeze drying techniques, which yield a powder of AST or a salt thereof, plus any additional desired ingredient present in the previously sterile-filtered solutions.

The compositions of the subject invention may also be administered orally, in combination with a pharmaceutically acceptable vehicle such as an inert diluent or an assimilable edible carrier. They may be enclosed in hard or soft shell gelatin capsules may be compressed into tablets, or may be incorporated directly with the food of the subject's diet.

For oral therapeutic administration, AST or a salt thereof may be combined with one or more excipients and used in the form of ingestible tablets, buccal tablets, troches, capsules, elixirs, suspensions, syrups, wafers, and the like. Such compositions and preparations should contain at least 0.1% of AST or a salt thereof of the present invention. The percentage of AST or a salt thereof present in such compositions and preparations may, of course, be varied and may conveniently be between about 2% to about 60% of the weight of a given unit dosage form. The amount of AST or a salt thereof in such therapeutically useful compositions is such that an effective dosage level will be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid, and the like; a lubricant such as magnesium stearate; and a sweetening agent such as sucrose, fructose, lactose, or aspartame, or a flavoring agent such as peppermint, oil of wintergreen, or cherry flavoring may be added.

When the unit dosage form is a capsule, it may contain, in addition to materials of the above type, a liquid carrier, such as a vegetable oil or a polyethylene glycol.

Various other materials may be present as coatings or for otherwise modifying the physical form of the solid unit dosage form. For instance, tablets, pills, or capsules may be coated with gelatin, wax, shellac, or sugar, and the like. A syrup or elixir may contain AST or a salt thereof, and sucrose or fructose as a sweetening agent, methyl and propylparabens as preservatives, a dye, and flavoring such as cherry or orange flavor.

Of course, any material used in preparing any unit dosage form should be pharmaceutically acceptable and substantially non-toxic in the amounts employed.

In addition, AST or a salt thereof may be incorporated into sustained-release preparations and devices. For example, AST or a salt thereof may be incorporated into time release capsules, time release tablets, time release pills, and time release polymers or nanoparticles.

Pharmaceutical compositions for topical administration of AST or a salt thereof to the epidermis (mucosal or cutaneous surfaces) can be formulated as ointments, creams, lotions, gels, or as a transdermal patch. Such transdermal patches can contain penetration enhancers such as linalool, carvacrol, thymol, citral, menthol, t-anethole, and the like. Ointments and creams can, for example, include an aqueous or oily base with the addition of suitable thickening agents, gelling agents, colorants, and the like. Lotions and creams can include an aqueous or oily base and typically also contain one or more emulsifying agents, stabilizing agents, dispersing agents, suspending agents, thickening agents, coloring agents, and the like. Gels preferably include an aqueous carrier base and include a gelling agent such as cross-linked polyacrylic acid polymer, a derivatized polysaccharide (e.g., carboxymethyl cellulose), and the like.

Useful solid carriers include finely divided solids such as talc, clay, microcrystalline cellulose, silica, alumina, and the like. Other solid carriers include nontoxic polymeric nanoparticles or microparticles. Useful liquid carriers include water, alcohols, or glycols, or water/alcohol/glycol blends, in which AST or a salt thereof can be dissolved or dispersed at effective levels, optionally with the aid of non-toxic surfactants. Adjuvants such as fragrances and additional antimicrobial agents can be added to optimize the properties for a given use.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like.

The concentration of AST or a salt thereof in such formulations can vary widely depending on the nature of the formulation and intended route of administration. For example, the concentration of AST or a salt thereof in a liquid composition, such as a lotion, can preferably be from about 0.1-25% by weight, or, more preferably, from about 0.5-10% by weight. The concentration in a semi-solid or solid composition such as a gel or a powder can preferably be about 0.1-5% by weight, or, more preferably, about 0.5-2.5% by weight.

Pharmaceutical compositions for spinal administration or injection into amniotic fluid can be provided in unit dose form in ampoules, pre-filled syringes, small volume infusion, or in multi-dose containers, and can include an added preservative. The compositions for parenteral administration (e.g., by injection, for example bolus injection or continuous infusion) can be suspensions, solutions, or emulsions, and can contain excipients such as suspending agents, stabilizing agents, and dispersing agents.

Pharmaceutical compositions suitable for intra-nasal administration are also encompassed by the present invention. Such intra-nasal compositions comprise AST or a salt thereof in a vehicle and suitable administration device to deliver a liquid spray, dispersible powder, or drops. Drops may be formulated with an aqueous or non-aqueous base also comprising one or more dispersing agents, solubilizing agents, or suspending agents. Liquid sprays are conveniently delivered from a pressurized pack, an insufflator, a nebulizer, or other convenient means of delivering an aerosol comprising AST or a salt thereof. Pressurized packs comprise a suitable propellant such as dichlorodifluoromethane, trichlorofluoromethane, dichlorotetrafluoroethane, carbon dioxide, or other suitable gas as is well known in the art. Aerosol dosages can be controlled by providing a valve to deliver a metered amount of AST or a salt thereof.

AST or a salt thereof may be combined with an inert powdered carrier and inhaled by the subject or insufflated. Pharmaceutical compositions for administration by inhalation or insufflation can be provided in the form of a dry powder composition, for example, a powder mix of AST or a salt thereof and a suitable powder base such as lactose or starch. Such powder composition can be provided in unit dosage faun, for example, in capsules, cartridges, gelatin packs, or blister packs, from which the powder can be administered with the aid of an inhalator or insufflator.

The exact amount (effective dose) of AST or a salt thereof can vary from subject to subject, depending on, for example, the species, age, weight, and general or clinical condition of the subject, the severity or mechanism of any disorder being treated, the particular agent or vehicle used, the method and scheduling of administration, and the like. A therapeutically effective dose can be determined empirically, by conventional procedures known to those of skill in the art. See, e.g., The Pharmacological Basis of Therapeutics, Goodman and Gilman, eds., Macmillan Publishing Co., New York. For example, an effective dose can be estimated initially either in cell culture assays or in suitable animal models. The animal model may also be used to determine the appropriate concentration ranges and routes of administration. Such information can then be used to determine useful doses and routes for administration in humans. Methods for the extrapolation of effective dosages in mice and other animals to humans are known to the art; for example, see U.S. Pat. No. 4,938,949, which is hereby incorporated by reference. A therapeutic dose can also be selected by analogy to dosages for comparable therapeutic agents.

The particular mode of administration and the dosage regimen will be selected by the attending clinician, taking into account the particulars of the case (e.g., the subject, the disease, the disease state involved, and whether the treatment is prophylactic). Treatment may involve daily or multi-daily doses of compound(s) over a period of a few days to months, or even years.

AST or salts thereof may conveniently be presented in a single dose or as divided doses administered at appropriate intervals, for example, as one dose per day or as two, three, four or more sub-doses per day. The sub-dose itself may be further divided, e.g., into a number of discrete loosely spaced administrations, such as multiple inhalations from an insufflator.

Optionally, the pharmaceutical compositions of the present invention can include one or more other therapeutic agents, e.g., as a combination therapy. The additional therapeutic agent(s) will be included in the compositions within a therapeutically useful and effective concentration range, as determined by routine methods that are well known in the medical and pharmaceutical arts. The concentration of any particular additional therapeutic agent may be in the same range as is typical for use of that agent as a monotherapy, or the concentration may be lower than a typical monotherapy concentration if there is a synergy when combined with AST or a salt thereof.

Methods of Use

The subject invention provides methods of treating, inhibiting, or preventing malaria infection in a subject in need thereof comprising administering the antimalarial agents/compounds or the composition of the subject invention to the subject in an amount effective to treat, inhibit, or prevent malaria infection in the subject. Advantageously, the antimalarial agent/compound (e.g., AST or a salt thereof) or the composition of the subject invention inhibits the malaria parasite (e.g., *Plasmodium*) without being toxic to other eukaryotes such as human cells.

The effective amount of said pharmaceutical composition can be administered through, for example, oral, rectal, bronchial, nasal, topical, buccal, sub-lingual, transdermal, vaginal, intramuscular, intraperitoneal, intravenous, intraarterial, intracerebral, interaocular administration or in a form suitable for administration by inhalation or insufflation, including powders and liquid aerosol administration, or by sustained release systems such as semipermeable matrices of solid hydrophobic polymers containing the compound(s) of the invention. Administration may be also by way of other carriers or vehicles such as patches, micelles, liposomes, vesicles, implants (e.g., microimplants), synthetic polymers, microspheres, nanoparticles, and the like.

In certain embodiments, the malaria parasite is selected from, for example, *P. falciparum, P. malariae, P. ovale, P. vivax, P. knowlesi, P. berghei, P. chabaudi* and *P. yoelii*. In specific embodiments, malaria is caused by, for example, Plasmodium (P.) species including, for example, *P. falciparum, P. malariae, P. ovale, P. vivax, P. knowlesi, P. berghei, P. chabaudi* and *P. yoelii*.

In one embodiment, the subject may be any animal including mammals, preferably, human. The subjects further include, but are not limited to, non-human primates, rodents (e.g., rats, mice), dogs, cats, horses, cattle, pigs, sheep, goats, chickens, guinea pigs, hamsters and the like.

In one embodiment, the subject invention provides a method for treating malaria in a subject suffering from malaria, wherein the method comprises administering an effective amount of an antimalarial agent/compound or a pharmaceutical composition comprising the antimalarial agent/compound to the subject. In a specific embodiment, the method for treating malaria in a subject comprises administering an effective amount of AST or a salt thereof, or a pharmaceutical composition comprising AST or a salt thereof to the subject.

In one embodiment, the subject invention provides a method for inhibiting, reducing or preventing malaria transmission from a subject to mosquitos, where the method comprises administering, to the subject, an effective amount of an antimalarial agent/compound or a pharmaceutical composition comprising the antimalarial agent/compound.

In a specific embodiment, the subject invention provides a method for inhibiting, reducing or preventing malaria transmission from a subject to mosquitos, where the method comprises administering, to the subject, an effective amount of AST or a salt thereof, or a pharmaceutical composition comprising AST or a salt thereof.

Also provided is a method for inhibiting the proliferation of the asexual-stage malaria parasite, such as *P. falciparum*, by using the antimalarial agents/compounds, or the composition comprising the antimalarial agents/compounds. In certain embodiments, the method for inhibiting the proliferation of the asexual-stage malaria parasite in a subject, comprises administering, to the subject, an antimalarial agent/compound or a pharmaceutical composition comprising the antimalarial agent/compound. In a specific embodiment, the antimalarial agent/compound inhibits the proliferation of asexual-stage malaria parasites in red blood cells.

In certain embodiments, the method for inhibiting the proliferation of the asexual-stage malaria parasite in a subject, comprises administering, to the subject, an effective amount of AST or a salt thereof or a pharmaceutical composition comprising AST or a salt thereof.

In certain embodiments, the subject invention provides a method for inhibiting the transmission of sexual-stage malaria parasite, such as *P. falciparum*, the method comprising administering, to a subject, an antimalarial agent/compound or a pharmaceutical composition comprising the antimalarial agent/compound.

In specific embodiments, the method for inhibiting the transmission of sexual-stage malaria parasite, such as *P. falciparum*, comprises administering, to a subject, an effective amount of AST or a salt thereof, or a pharmaceutical composition comprising AST or a salt thereof.

In certain embodiments, the subject invention provides a method for reducing parasitemia in a subject, the method comprising administering, to the subject, an antimalarial agent/compound or a pharmaceutical composition comprising the antimalarial agent/compound.

In specific embodiments, the method for reducing parasitemia in a subject comprises administering, to the subject, an effective amount of AST or a salt thereof, or a pharmaceutical composition comprising AST or a salt thereof.

In certain embodiments, the subject invention provides a method for inhibiting GS, or type-I GS (GS-I) of malaria parasite, such as *P. falciparum* GS (PfGS-I), the method comprising administering, to a subject, an antimalarial agent/compound or a pharmaceutical composition comprising the antimalarial agent/compound, wherein the subject has been infected with malaria parasite, such as *P. falciparum*.

In specific embodiments, the method for inhibiting GS, or type-I GS (GS-I) of malaria parasite, such as PfGS-I, comprises administering, to a subject, an effective amount of AST or a salt thereof, or a pharmaceutical composition comprising AST or a salt thereof.

In some embodiments, the antimalarial agent/compound can be administered in combination with another therapeutic agent for malaria, wherein such therapeutic agents include, for example, atovaquone-proguanil (Malarone), quinine sulfate (Qualaquin), doxycycline, Primaquine phosphate, chloroquine, mefloquine, and tafenoquine.

In one embodiment, a suitable dose will be in the range of from about 0.001 to about 100 mg/kg of body weight per day, preferably from about 0.01 to about 100 mg/kg of body weight per day, more preferably, from about 0.1 to about 50 mg/kg of body weight per day, or even more preferred, in a range of from about 1 to about 10 mg/kg of body weight per day. For example, a suitable dose may be about 1 mg/kg, 10 mg/kg, or 50 mg/kg of body weight per day. AST, or salts thereof can be conveniently administered in unit dosage form, containing for example, about 0.05 to about 10000 mg, about 0.5 to about 10000 mg, about 5 to about 1000 mg, or about 50 to about 500 mg of each of AST, or salts thereof.

The antimalarial agent/compound can be administered to achieve peak plasma concentrations of, for example, from about 0.005 to about 200 µM, from about 0.01 to about 150 µM, from about 0.02 to about 100 µM, from about 0.02 to about 80 µM, from about 0.05 to about 50 µM, from about 0.05 to about 20 µM, from about 0.05 to about 10 µM, from about 0.05 to about 5 µM, from about 0.05 to about 1 µM, from about 0.1 to about 100 µM, from about 0.5 to about 75 µM, from about 1 to about 50 µM, from about 2 to about 30 µM, or from about 5 to about 25 µM.

Exemplary desirable plasma concentrations include at least 0.25, 0.5, 1, 5, 10, 25, 50, 75, 100 or 200 µM. For example, plasma levels may be from about 1 to about 100 micromolar or from about 10 to about 25 micromolar. This may be achieved, for example, by the intravenous injection of a 0.05 to 5% solution of AST or salts thereof, optionally in saline, or orally administered as a bolus containing about 1 to about 100 mg of AST, or salts thereof. Desirable blood levels may be maintained by continuous or intermittent infusion.

Examples of mosquito genera include, but are not limited to *Aedeomyia*, *Aedes*, *Anopheles*, *Armigeres*, *Ayurakitia*, *Borachinda*, *Coquillettidia*, *Culex*, *Culiseta*, *Deinocerites*, *Eretmapodites*, *Ficalbia*, *Galindomyia*, *Haemagogus*, *Heizmannia*, *Hodgesia*, *Isostomyia*, *Johnbelkinia*, *Kimia*, *Limatus*, *Lutzia*, *Malaya*, *Mansonia*, *Maorigoeldia*, *Mimomyia*, *Onirion*, *Opifex*, *Orthopodomyia*, *Psorophora*, *Runchomyia*, *Sabethes*, *Shannoniana*, *Topomyia*, *Toxorhynchites*, *Trichoprosopon*, *Tripteroides*, *Udaya*, *Uranotaenia*, *Verrallina*, and *Wyeomyia*. In one embodiment, the mosquito is an *Anopheles* spp., *Aedes* spp., *Culex* spp., *Culiseta* spp., *Haemagogus* spp. Preferably, the mosquito may be *Anopheles* spp.

In a further embodiment, the Anopheles spp. may be *An. arabiensis*, *An. funestus*, *An. gambiae*, *An. moucheti*, *An. nili*, *An. stephensi*, *An. bellator*, *An. cruzii*, *An. farauti* or a combination of two or more thereof. Preferably, the *Anopheles* spp. may be *An. gambiae*. Examples of the *Anopheles* species include *Anopheles (Cellia) aconitus*; *Anopheles (Nyssorhynchus) albimanus*; *Anopheles (Nyssorhynchus) albitarsis* species complex; *Anopheles (Cellia) annularis*; *Anopheles (Nyssorhynchus) aquasalis*; *Anopheles (Cellia) arabiensis*; *Anopheles (Anopheles) atroparvus*; *Anopheles (Cellia) balabacensis*; *Anopheles (Anopheles) barbirostris* species complex; *Anopheles (Cellia) culicifacies* species complex; *Anopheles (Nyssorhynchus) darling*; *Anopheles (Cellia) dirus* species complex; *Anopheles (Cellia) farauti* species complex; *Anopheles (Cellia) flavirostris*; *Anopheles (Cellia) fluviatilis* species complex; *Anopheles (Anopheles) freeborni*; *Anopheles (Cellia) funestus*; *Anopheles (Cellia) gambiae*; *Anopheles (Cellia) koliensis*; *Anopheles (Anopheles) labranchiae*; *Anopheles (Anopheles) lesteri* (formerly *An. anthropophagus* in China); *Anopheles (Cellia) leucosphyrus* and *Anopheles (Cellia) latens*; *Anopheles (Cellia) maculatus* Group; *Anopheles (Nyssorhynchus) marajoara*; *Anopheles (Cellia) melas*; *Anopheles (Cellia) merus*; *Anopheles (Anopheles) messeae*; *Anopheles (Cellia) minimus* species complex; *Anopheles (Cellia) moucheti*; *Anopheles (Cellia) nili* species complex; *Anopheles (Nyssorhynchus) nuneztovari* species complex; *Anopheles (Anopheles) pseudopunctipennis* species complex; *Anopheles (Cellia) punctulatus* species complex; *Anopheles (Anopheles) quadrimaculatus*; *Anopheles (Anopheles) sacharovi*; *Anopheles (Cellia) sergentii* species complex; *Anopheles (Anopheles) sinensis* species complex; *Anopheles (Cellia) stephensi*; *Anopheles (Cellia) subpictus* species complex; *Anopheles (Cellia) sundaicus* species complex,. *Anopheles (Cellia) superpictus*.

In an embodiment, the mosquito is female.

In a specific embodiment, the human has been diagnosed with malaria or is suffering from malaria.

The subject invention also provides methods for treating a subject infected with malaria parasites or malaria parasite oocysts. Further provided in the subject invention are methods of preventing or reducing malaria transmission from a subject infected with a malarial parasite, comprising administering to the subject the antimalarial agent/compound or the composition of the subject invention.

In one embodiment, the administration to a subject can be via any convenient and effective route, such oral, rectal, nasal, topical, (including buccal and sublingual), transdermal, parenteral (including intramuscular, subcutaneous, and intravenous), spinal (epidural, intrathecal), and central (intracerebroventricular). Non-limiting embodiments include parenteral administration, such as by injection, e.g., into the blood stream, intradermal, intramuscular, etc., or mucosal administration, e.g., intranasal, oral, and the like.

In some embodiments, the method further comprises detecting the activity of GS of the malaria parasite.

In one embodiment, the inhibition/reduction is at least about 5%, at least about 10%, at least about 15%, at least about 20%, at least about 25%, at least about 30%, at least about 35%, at least about 40%, at least about 45, at least about 50%, at least about 55%, at least about 60%, at least about 65%, at least about 70%, at least about 75%, at least about 80%, at least about 85%, at least about 90%, at least about 95%, at least about 99%, at least about 99.5%, or any percentage in between. In a preferred embodiment, the inhibition is 99.9% or 100%.

Definitions

The term "subject" refers to an animal, such as a mammal, for example a human. The methods described herein can be useful in both pre-clinical human therapeutics and veterinary applications. In some embodiments, the subject is a mammal (such as an animal model of disease), and in some embodiments, the subject is human. Non-limiting examples of subjects include canine, porcine, rodent, feline, bovine, poultry, equine, human, and a non-human primate.

As used herein, "antimalarial agent," refers to AST or a salt thereof. The salts can be with an inorganic acid, such as hydrochloric acid, hydrobromic acid, perchloric acid, nitric acid, thiocyanic acid, sulfuric acid, and phosphoric acid; an organic acid, such as trifluoroacetic acid (TFA), formic acid, acetic acid, propionic acid, glycolic acid, lactic acid, pyruvic acid, oxalic acid, malonic acid, succinic acid, maleic acid, and fumaric acid; or a salt with a base, such as sodium hydroxide, ammonium hydroxide, potassium hydroxide, and organic bases such as mono-, di-, trialkyl and aryl amines, and substituted ethanolamines.

Further salts include: (1) acid addition salts, formed with inorganic acids such as sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-di sulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in AST or salts thereof is either replaced by a metal ion, e.g., an alkali metal ion, an alkaline earth ion, a selenium ion or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like.

"Pharmaceutically acceptable carrier" refers to a diluent, adjuvant or excipient with which the antigen disclosed herein can be formulated. Typically, a "pharmaceutically acceptable carrier" is a substance that is non-toxic, biologically tolerable, and otherwise biologically suitable for administration to a subject, such as an inert substance, added to a pharmacological composition or otherwise used as a diluent, or excipient to facilitate administration of the antigen disclosed herein and that is compatible therewith. Examples of excipients include various sugars and types of starches, cellulose derivatives, gelatin, vegetable oils, and polyethylene glycols. Additional examples of carriers suitable for use in the pharmaceutical compositions are known in the art and such embodiments are within the purview of the invention.

Examples of carriers suitable for use in the pharmaceutical compositions are known in the art and such embodiments are within the purview of the invention. The pharmaceutically acceptable carriers and excipients, including, but not limited to, aqueous vehicles, water-miscible vehicles, non-aqueous vehicles, stabilizers, solubility enhancers, isotonic agents, buffering agents, suspending and dispersing agents, wetting or emulsifying agents, complexing agents, sequestering or chelating agents, cryoprotectants, lyoprotectants, thickening agents, pH adjusting agents, and inert gases. Other suitable excipients or carriers include, but are not limited to, dextran, glucose, maltose, sorbitol, xylitol, fructose, sucrose, and trehalose.

The term "amount effective," "effective amount" or "therapeutically effective amount" as used herein, refers to an amount that is capable of treating or ameliorating a disease or condition or otherwise capable of producing an intended therapeutic effect. The therapeutically effective amount may vary depending upon the intended application, the subject, and the infection being treated, e.g., the weight and age of the subject, the severity of the infection, the manner of administration and the like, which can readily be determined by one of ordinary skill in the art. In certain embodiments, the effective amount enables at least 5%, 10%, 15%, 20%, 25%, 30%, 35%, 40%, 45%, 50%, 60%, 70%, 80%, 90%, or 100% inhibition of malaria infection and transmission.

The term "prevention" or any grammatical variation thereof (e.g., prevent, preventing, etc.), as used herein, includes but is not limited to, at least the reduction of likelihood of the risk of (or susceptibility to) acquiring a disease or disorder (i.e., causing at least one of the clinical symptoms of the disease not to develop in a patient that may be exposed to or predisposed to the disease but does not yet experience or display symptoms of the disease). The term "prevention" may refer to avoiding, delaying, forestalling, or minimizing one or more unwanted features associated with a disease or disorder, and/or completely or almost completely preventing the development of a disease or disorder and its symptoms altogether. Prevention can further include, but does not require, absolute or complete prevention, meaning the disease or disorder may still develop at a later time and/or with a lesser severity than it would without preventative measures. Prevention can include reducing the severity of the onset of a disease or disorder, and/or inhibiting the progression thereof.

The terms "treatment" or any grammatical variation thereof (e.g., treat, treating, etc.), as used herein, includes but is not limited to, the application or administration to a subject (or application or administration to a cell or tissue from a subject) with the purpose of delaying, slowing, stabilizing, curing, healing, alleviating, relieving, altering, remedying, less worsening, ameliorating, improving, or affecting the disease or condition, the symptom of the disease or condition, or the risk of (or susceptibility to) the disease or condition. The term "treating" refers to any indication of success in the treatment or amelioration of a pathology or condition, including any objective or subjective parameter such as abatement; remission; lessening of the rate of worsening; lessening severity of the disease; stabilization, diminishing of symptoms or making the pathology or condition more tolerable to the subject; or improving a subject's physical or mental well-being.

The terms "co-administration," "administered in combination with," and their grammatical equivalents encompass administration of two or more agents to a subject so that both agents and/or their metabolites are present in the subject at the same time. Co-administration includes simultaneous administration in separate compositions, administration at different times in separate compositions, or administration in a composition in which both agents are present. Co-administered agents may be in the same formulation. Co-administered agents may also be in different formulations.

As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof) "comprising," "comprises," and "comprise" can be used interchangeably; "consisting essentially of," and "consists essentially of" can be used interchangeably; and "consisting," and "consists" can be used interchangeably.

The transitional term "comprising," "comprises," or "comprise" is inclusive or open-ended and does not exclude additional, unrecited elements or method steps. By contrast, the transitional phrase "consisting of" excludes any element, step, or ingredient not specified in the claim. The phrases "consisting" or "consists essentially of" indicate that the claim encompasses embodiments containing the specified materials or steps and those that do not materially affect the basic and novel characteristic(s) of the claim. Use of the term "comprising" contemplates other embodiments that "consist" or "consisting essentially of" the recited component(s).

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Where particular values are described in the application and claims, unless otherwise stated the term "about" meaning within an acceptable error range for the particular value should be assumed.

When ranges are used herein, such as for dose ranges, percentage, combinations and subcombinations of ranges (e.g., subranges within the disclosed range), specific embodiments therein are intended to be explicitly included.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly used dictionaries, should be interpreted as having a meaning that is consistent with their meaning in the context of the relevant art and/or as otherwise defined herein.

EXAMPLES

Materials and Methods

Reagents

Unless otherwise stated, reagents and enzymes were all from MilliporeSigma (Burlington, MA). AST was chromatographically purified from large-scale cultures of *B. gladioli* GSRB05. The concentration of purified AST was determined by inductively coupled plasma mass spectrometry (ICP-MS) (NexION 1000; Perkin-Elmer, Waltham, MA, USA), while the purity was confirmed by high-pressure liquid chromatography (NexSAR HPLC system, Perkin-Elmer)-coupled to ICP-MS (HPLC-ICP-MS). The purified AST is the L-enantiomeric form. Sodium (meta)arsenite, sodium arsenate, disodium methylarsenate and sodium cacodylate were used as arsenite (As(III)), arsenate (As(V)), methylarsenate (MAs(V)) and dimethylarsenate (DMAs(V)). Methylarsenite (MAs(III)), hydroxyarsinothricin (AST-OH), monothio-methylarsenate (T-MAs(V)) and monothio-dimethylarsenate (T-DMAs(V)) were prepared.

Mosquitos and Plasmodium Strains

Mosquito eggs (G3) were obtained through BEI Resources (Manassas, VA). After hatching, the mosquito colonies were maintained at 27° C. in BSL-2 insectary with a 12 h day-night cycle and 80% humidity. *Plasmodium falciparum* (NE54) parasites were obtained from BEI Resources and maintained using fresh O+ human blood and AB+ serum purchased from a blood bank (continental blood bank, Miami, FL).

Human Cell Lines

Human cell lines from the major tissues/organs, e.g., HepG2 from the liver, HEK293 from the kidney, Caco-2 from the colon, THP-1 from blood monocyte, and macrophage derived from THP-1, were used to test cytotoxicity, cellular permeability and stability of AST. The cell lines were obtained from the American Type Culture Collection (ATCC) (Manassas, VA). All cells were cultured in their respective media suggested by the vendors in a 5% $CO_2$ humidified incubator at 37° C.

Phylogenetic Analysis of Glutamine Synthetase Homologs

*Escherichia coli* GS type I (NCBI Accession Number: WP_001726606), Homo sapiens GS type II (KAI2520623) and *Rozella allomycis* CSF55 GS type III (EPZ33612), representing each of the GS types, were used as queries to search for GS homologs using NCBI (National Center for Biotechnology Information) Protein Basic Local Alignment Search Tool (BLASTP) with default settings with a high score threshold of 200. GS homologs were searched in representative parasitic members in major eukaryotic phyla/divisions available in the "Organism" option of BLASTP. Among the identified GS homologs, the following were selected as representatives for phylogenetic analysis: *P. falciparum* NF54 (EWC85923), *P. knowlesi* strain H (XP_038969575), *P. ovale* curtisi (SBS90972), *P. malariae* (XP_028860811), *P. vivax* (XP_001614758), *P. berghei* ANKA (XP_034421207), *Babesia microti* strain RI (XP_012648738), *Toxoplasma gondii* ME49 (XP_002365950), *Eimeria tenella* (XP_013228270), *Cyclospora cayetanensis* (XP_026191025), *Cryptosporidium parvum* Iowa II (XP_627788), *Perkinsus marinus* ATCC 50983 (XP_002779778 and XP_002788110), *Plasmodiophora brassicae* (CEP01483), *Phytophthora kernoviae* 00238/432 (KAF4321638 and KAF4314669), *Blastocystis* sp. ATCC 50177 (OAO13151), *Trypanosoma cruzi* (EKG07062), *T. brucei gambiense* DAL972 (XP_011774949), *Leishmania donovani* (AMQ34913), *L.*

*mexicana* MHOM (XP_003872049), *L. major* strain Friedlin (CAG9568830), *Entamoeba histolytica* KU27 (EMD47977), *Trichomonas vaginalis* G3 (XP_001311020), *Histoplasma capsulatum* H143 (EER45446), *Cryptococcus gattii* WM276 (XP_003191404), *Candida albicans* SC5314 (XP_711992) and *Aspergillus fumigatus* (KAF4291211). In addition to these GS sequences, several more GS homologs were selected from each type as follows: GS-I: *Desulfurococcus amylolyticus* (WP_014766917), *Nostoc punctiforme* (WP_012411650), *Mycobacterium tuberculosis* (WP_003411475), *Bacillus subtilis* (WP_014479846), *Arabidopsis thaliana* (NP_190886), *Oryza sativa* (XP_015614516), *Danio rerio* (NP_001026844), *Ustilago bromivora* (SAM83183), *Thalassiosira pseudonana* CCMP1335 (XP_002288024); GS-II: *Verrucomicrobia bacterium* (RME72265), *Cystobacter fuscus* (WP_095991499), *Arabidopsis thaliana* (NP_188409), *Oryza sativa* (NP_001388898), *Volvox carteri f. nagariensis* (XP_002956198), *Drosophila melanogaster* (NP_001162839), *Saccharomyces cerevisiae* S288C (NP_015360), *Thalassiosira pseudonana* CCMP1335 (XP_002294945); GS-III: methanogenic archaeon ISO4-H5 (AMH93813), *Synechococcus* sp. CS-197 (WP_011933362), *Cryobacterium arcticum* (WP_066594742), *Clostridium beijerinckii* (WP_077844654), *Chlorobium phaeobacteroides* (WP_011744711), *Dyadobacter fermentans* (WP_012780063), *Flavobacterium psychrophilum* (WP_011962708), *Ostreococcus lucimarinus* CCE9901 (XP_001415954), *Thalassiosira pseudonana* CCMP1335 (XP_002295274). Phylogenetic analysis was performed to infer the evolutionary relationship among the sequences of GS from various organisms. The phylogenetic tree was constructed by MEGA XI as illustrated with ClustalW and Neighbor-Joining used for sequence alignment and phylogeny estimation, respectively, where the statistical significance of the branch pattern was estimated from a 1000 bootstrap. Multiple sequence alignment of selected GS was performed using Clustal Omega (www.ebi.ac.uk/Tools/msa/clustalo/, accessed on 30 Apr. 2023).

Cloning, Expressing, and Purifying Proteins

PfglnA encoding GS-I from *P. falciparum* (NF54) (accession number: EWC85923.1), a 1626-bp fragment including the stop codon with codon optimization for expression in *E. coli*, was chemically synthesized by GenScript (Piscataway, NJ, USA) with NdeI and EcoRI at 5' and 3' sites, respectively, and cloned into pMAL-c5x, generating plasmid pMAL-PfglnA. *E. coli* BL21(DE3) cells bearing pMAL-PfglnA were grown in lysogeny broth (LB) medium supplemented with 25 µM ampicillin at 37° C. with shaking at 200 rpm. At an $A_{600nm}$ of 0.5-0.6, Isopropyl ß-D-1-thiogalactopyranoside and glycerol were added at final concentrations of 10 µM and 0.5% (v/v), respectively. After incubation with shaking at 16° C. overnight, the cells were harvested and stored at −80° C. until use. The frozen cells were thawed and resuspended in buffer A (50 mM morpholinopropane-1-sulfonic acid (MOPS), 1 mM tris(2-carboxyethyl)phosphine, pH 7.5, 0.5 M NaCl and 20% (v/v) glycerol) (5 ml per g of wet cells). The cells were lysed by a single passage through a French pressure cell at 20,000 psi, and the cell lysate was centrifuged at 40,000 rpm using a T865 rotor (Thermo Fisher Scientific, Waltham, MA, USA) for 60 min at 4° C. The supernatant solution was applied onto an amylose resin column (New England BioLabs, Ipswich, MA) at a flow rate of 1.0 ml/min and washed until no protein was detected from the flow-through using the method of Bradford. Bound protein was eluted with buffer A containing 10 mM maltose, and the purity was analyzed by SDS-PAGE. Protein concentrations were estimated by the method of Bradford with bovine serum albumin used as a standard. Fractions containing the target protein were pooled and concentrated using a 30 kDa Amicon Ultra centrifugal filter (MilliporeSigma). The concentrated protein was rapidly frozen and stored at −80° C. until use.

Glutamine Synthetase Assays

The activity and inhibition profiles of purified MBP-fused PfGS-I or human GS-II (hGS-II) (BioVision Inc., Milpitas, CA, USA) in the presence or absence of AST were estimated from glutamine production using Glutamine/Glutamate-GLO™ Assay Kit (Promega, Madison, WI). The assay mixture (50 mM imidazole-HCl buffer (pH 7.0), 7.6 mM ATP, 50 mM magnesium chloride, 50 mM ammonium chloride) with or without the indicated concentration of GS enzyme was preincubated in the presence or absence of the indicated concentrations of AST for 15 min at room temperature. The reaction was initiated by addition of L-glutamate at 0.1 mM, final concentration. The reaction mixtures were incubated at 37° C. with shaking at 300 rpm for indicated time. The reactions were terminated by chilling the reaction mixture in ice water and filtered with 30 kDa Amicon Ultra centrifugal filters at 4° C. Glutamate concentrations in the filtered samples were determined using Glutamine/Glutamate-GLO™ Assay as instructed in the kit's manual, from which glutamine concentrations were estimated by subtracting the glutamate concentrations from the initial concentrations (0.1 mM). The half maximal effective concentration ($EC_{50}$) of AST for PfGS-I was calculated using Sigma Plot (Systat Software, Inc., San Jose, CA).

Antimalarial Activity of AST on the Asexual Stage of *P. falciparum*

3-5-day cultured *P. falciparum*-infected red blood cells (iRBCs) were mixed with fresh human RBCs (AB+ type) in complete RPMI 1640 to prepare cultures with 0.5% parasitemia and 2% hematocrit. AST was dissolved in DMSO. 5 µL DMSO with AST at concentrations of 0, 0.5, 1, 2, 4, and 8 mM were added to the 0.5 mL iRBCs in a 48-well plate, yielding final concentrations of 5, 10, 20, 40, and 80 µM, respectively. The plate was incubated in a candle jar at 37° C. Approximately 48 h later, the medium was replaced with fresh medium containing the same concentration of AST. Parasitemia was recorded on day 4 post-incubation.

Transmission-Blocking Assays of AST Against *P. falciparum*

*P. falciparum* (NF54) was cultured in the complete RPMI-1640 containing 4% new O+ human red blood cells, 10% human AB+ serum, and 12.5 µg/ml of hypoxanthine in a candle jar at 37° C. Standard membrane feeding assays (SMFA) were used to examine the efficacy of AST. In brief, 10 ml of day-15 cultured *P. falciparum* containing ~2% stage V gametocytes in a 15 ml centrifuge tube was centrifuged at 650×g for 5 min at RT. After the supernatant was removed, the cells were re-suspended in 1 ml of pre-warmed human AB− serum (37° C.), to which 1 ml of O+ hematocrit was added. 300 µl of the resulting infected blood were mixed with 2 µl of AST at different concentrations, yielding a final concentration of 0, 0.1, 0.3, 1, or 3 µM, which was fed a hundred 3-5-day-old female mosquitoes for 30 minutes. The unfed mosquitoes were removed, and the engorged mosquitoes were maintained with 10% sugar in the insectary. Seven days post-infection, the midguts were dissected and stained with 0.1% mercury dibromofluorescein salt in PBS for 30 minutes. The number of oocysts was counted under a 10× light microscope.

Cytotoxicity Assays

THP-1 cells were seeded in a 24-well plate at a density of $1.0 \times 10^5$ cells/well, while the other cell types were seeded at a density of $3.0 \times 10^5$ cells/well in 96-well plates. After 24 h, cells were further cultured in the presence or absence of the indicated concentrations of AST or As(III) for another 72 h, following which viability of cells was determined by a 3-(4,5-dimethylthiazol-2-yl) 2,5-diphenyltetrazolium bromide (MTT) assay. MTT was added to each well at a final concentration of 0.5 mg/mL, and the cultures were incubated for 3 h. The plate of THP-1 cells was then centrifuged at 400×g; the cell pellets were lysed with 300 μl of dimethyl sulfoxide to dissolve MTT formazan. For the other cell types, the MTT-containing medium was removed from each well, following which 50 μL of DMSO was added to solubilize the formazan. The cell viability was measured using $A_{570\ nm}$.

Membrane Permeability and Stability of AST in Human Cell Lines

The above-mentioned cell types were seeded at the density of $2.0 \times 10^6$ cells/well in 12-well plates and incubated with or without 100 μM AST in their respective media for 48 h. The culture media were collected for arsenic speciation. After washing four times with PBS, cells were collected with cell scrapers or centrifuge (400×g) and dried at room temperature for 48 h. For measurement of cellular permeability, the dried cells were digested with 70% nitric acid (≥99.999% trace metals basis) at 70° C. for 60 min, allowed to cool to room temperature and diluted to a final concentration of 2% nitric acid with HPLC-grade water, and the total arsenic content of each sample was quantified by ICP-MS. For analysis of intracellular AST stability, the dried cell pellets were resuspended in 10 mM Tris-NO3 (pH 7.4) (2.5 mL per 1 mg of dry cells). The cells were lysed by sonication on ice using a sonic dismembrator (Model 120, ThermoFisher Scientific) with 20% power in 20 s on-5 s off cycles for a total of 3 min. The cell lysates were centrifuged at 16,200×g at 4° C. for 10 mM, and the resulting supernatants were filtered with 3 kDa Amicon Ultra centrifugal filters at 4° C. The collected culture media were also filtered in the same fashion. Arsenic species in the filtered samples were analyzed by HPLC-ICP-MS using a reverse-phase C18 column (BioBasic™ 18 (particle size, 5 μm; length, 250 mm×4,6 mm)) (ThermoFisher Scientific). A standard solution containing As(III), As(V), MAs(I11), MAs(V), T-MAs(V), DMAs(V), T-DMAs(V), AST and AST-OH was freshly prepared and run at the beginning and/or end of each batch of sample analysis.

GS-AST Docking

The AST molecule taken from Protein Data Bank (PDB) entry 5WPH was docked with the cryogenic electron microscopy (cryoEM) structure of PfGS-I (PDB ID: 6PEW) using AutoDock4. The grid center was positioned on the glutamate-binding site of PfGS-I with a dimension of 40×40×40 Å$^3$ with default settings. The top-ranked confirmation was selected for further analysis. The same method was used for hGS-II (PDB ID: 2QC8). The molecular graphics were drawn using PyMol (Version 1.8, Schrödinger, Inc., New York, NY, USA).

Statistics

Assays of glutamine synthetase, AST antimalarial activity, cytotoxicity, permeability, and stability were repeated at least three times as indicated. Data are presented as the mean±standard error (SE). Student's t-test was used to calculate the p values of drug effects on GS activity and malaria infection in blood. Wilcoxon-Mann-Whitney test was used to calculate the p values of drug effects on malaria oocysts.

Example 1—*Plasmodium* GS is Phylogenetically Closer to Prokaryotic GS (GS-I) than to Eukaryotic GSII

*Plasmodium* glutamine synthetase has not been examined as a target for antimalarial development. PlasmoDB (plasmodb.org/plasmo/app/), a functional genomic database for malaria parasites reveals that *P. falciparum* possesses only a single GS gene in the genome (Gene ID: PF3D7_0922600). There are three distinct groups of glutamine synthetases. Type I (GS-I, encoded by glnA) and type II (GS-II, glnII) are the predominant forms in prokaryotes and eukaryotes, respectively. Type III (GS-III, glnN) was recently recognized in a few prokaryotes and eukaryotes. A phylogenetic analysis of representative parasite GS from seven phyla and one division was conducted (FIG. 1). GS-II, the predominant form in eukaryotes, is found in three phyla and one division, and GS-III is found in four phyla. In contrast, GS-I, the predominant form in prokaryotes, is also present in the eukaryotic phylum Apicomplexa, including *Plasmodium* species. The single exception is *Perkinsus marinus* in the phylum Perkinsozoa. The results demonstrate that *Plasmodium* GS belongs to the GS-I family. This is consistent with the recent cryoEM structure of PfGS, which shows that it is structurally similar to *Salmonella enterica* GS-I, forming a homo-dodecameric complex that adopts a two-tiered ring shape with hexametric symmetry.

Example 2—PfGS-I is a Functional GS

Prokaryotic GS-I proteins found in some eukaryotes frequently display no GS catalytic activity and may have different functions. In humans, for example, most tissues/organs express only catalytically-active GS-II. In contrast, human GS-I does not exhibit GS activity. It is expressed only in the lens of the eye and has designated lengsin (lens GS-like protein), probably with a structural role.

Figure 2A:
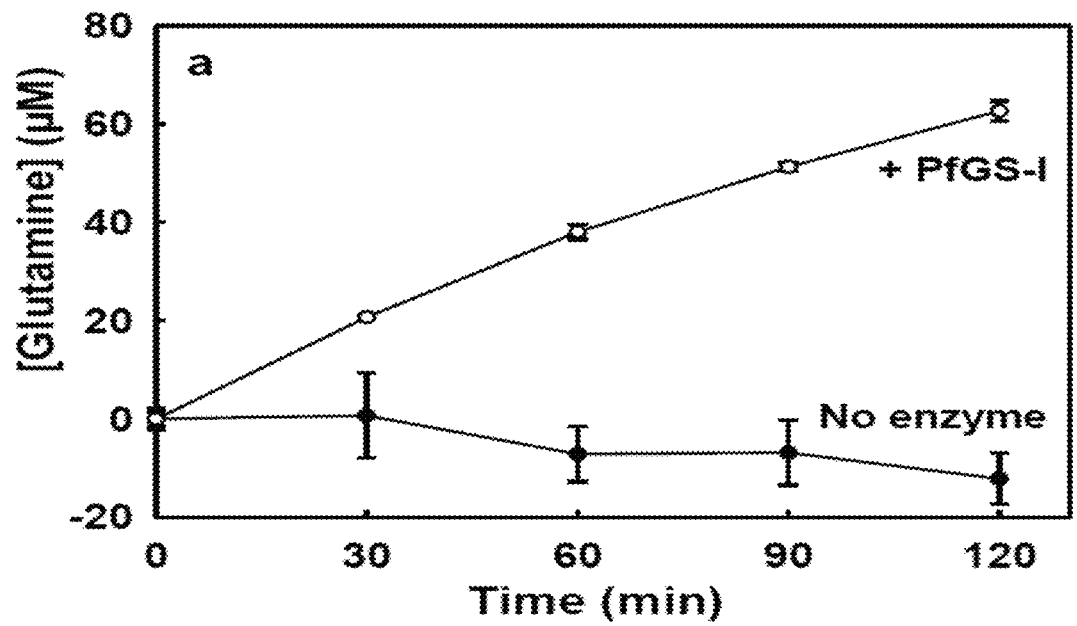
FIGS. 2A-2C show the inhibition of PfGS-I by AST. (2A) PfGS-I as a functional glutamine synthetase. The amount of glutamine produced from glutamate in the presence or absence of purified PfGS-I (0.5 µM) was measured every 30 min for 2 hours. (2B) AST effectively inhibits PfGS-I but not human GS-II. The amount of glutamine produced from glutamate by enzyme (1 µM) in the presence or absence of 1 µM AST in 30 min was measured. (2C) AST inhibits PfGS-I in a concentration-dependent manner. The activity of PfGS-I (0.5 µM) in the presence or absence of various concentrations of AST in 2 hours was measured. Data are the mean±SE (n=3). Student t-test was used to calculate the p values. Activities are normalized to the relative activity of untreated control reactions (1.0).

To examine the catalytic activity of PfGS-I, PfGS-I gene was cloned and expressed in *E. coli* and then GS activity of the purified protein was assayed. PfGS-I produced glutamine from glutamate in the presence of ATP, Mg$^{2+}$ and ammonia (FIG. 2A) demonstrates that PfGS-I is a functional GS.

Example 3—AST Effectively Inhibits PfGS-I but not Human GS-II

Figure 2B:
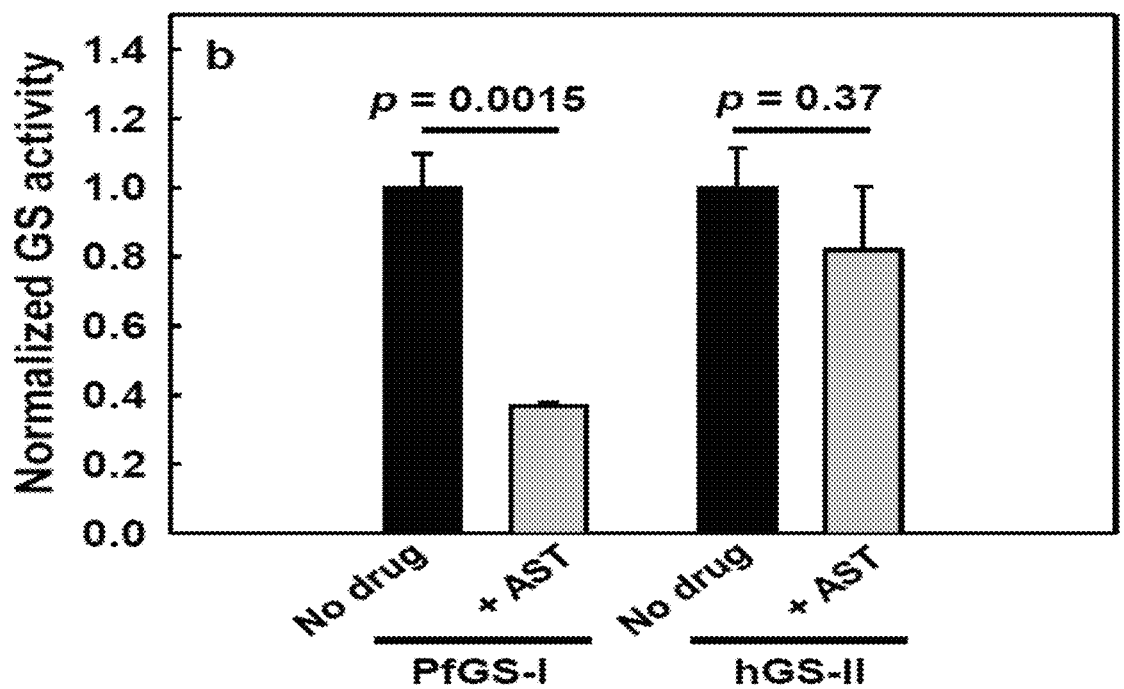
Figure 2C:
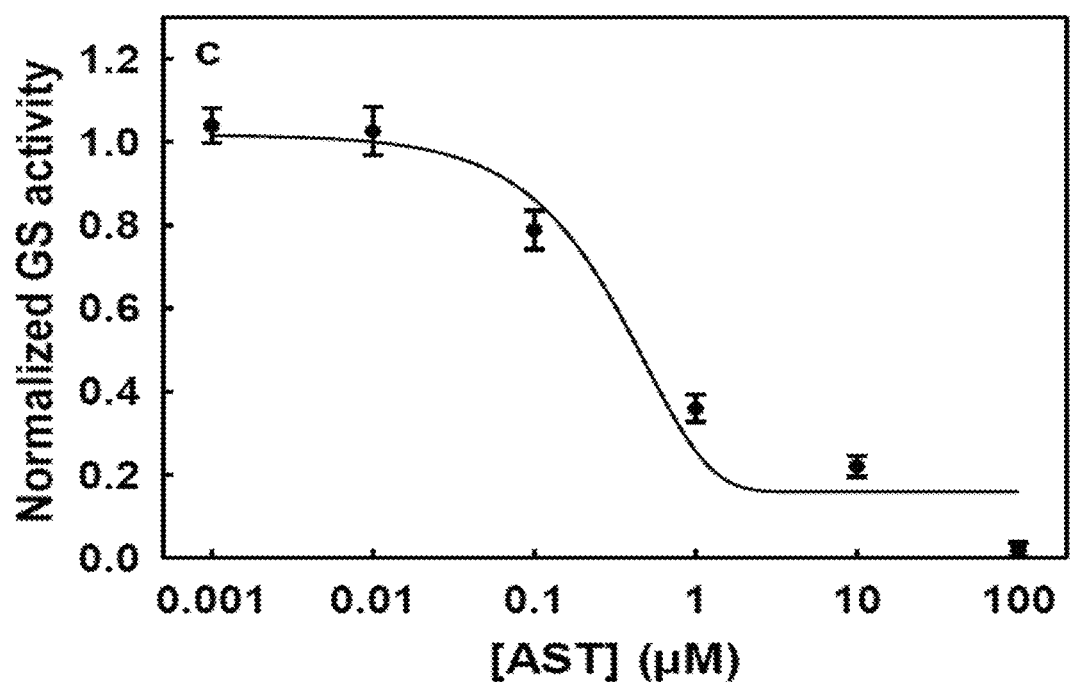

The inhibition activity of AST was examined on PfGS-I and compared with that on hGS-II. In the presence of 1 μM AST, the activity of PfGS-I (1 μM) was less than 40%, compared with the control without AST treatment (FIG. 2B). In contrast, 1 µM AST did not significantly reduce the activity of hGS-II (1 µM), suggesting that AST is much less effective on hGS-II. AST inhibited PfGS-I in a concentration-dependent manner (FIG. 2C), with an EC50 value in the sub-micromolar range (0.4 µM), demonstrating that AST is an effective PfGS-I inhibitor with high selectivity for PfGS-I over hGS-II.

Example 4—AST Inhibits Asexual-Stage *P. falciparum* Proliferation

Figure 3:
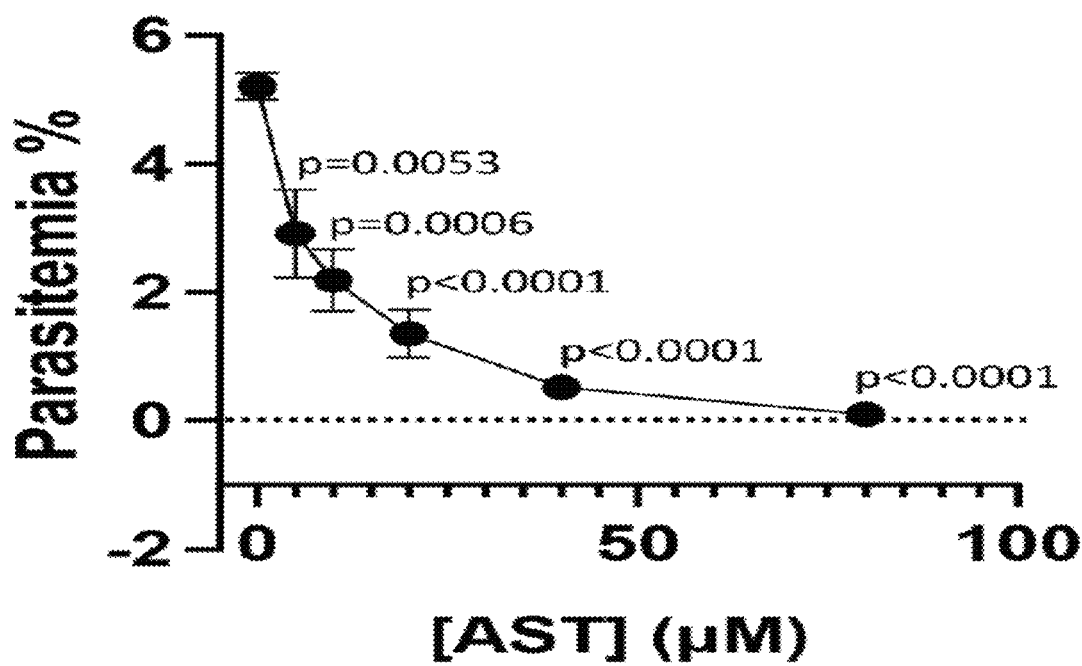
FIG. 3 shows that AST inhibits blood-stage P. falciparum proliferation. P. falciparum-infected erythrocytes with 0.5% parasitemia were incubated at 2% hematocrit in the presence or absence of the indicated concentrations of AST for 4 days, and parasitemia were determined, as described in Materials and methods. Data are the mean±SE (n=3). A one-way ANOVA test was used to calculate the p values.

Both transcriptomics and proteomics data indicate that PfGS-I is expressed throughout all stages of the malaria parasite life cycle (plasmodb.org/plasmo/app/record/gene/PF3D7_0922600#category:proteomics). To investigate whether AST might be a potent multi-stage antimalarial drug through the inhibition of PfGS-I, the effect of AST on *P. falciparum* proliferation was first examined in human blood. AST was added into *P. falciparum*-infected blood and measured parasitemia as the percentage of infected cells on day 4. The results showed that AST inhibits asexual-stage P. falciparum proliferation in the blood in a dose-dependent manner (FIG. 3). The $EC_{50}$ for AST in inhibiting the asexual-stage *P. falciparum*, defined as the concentration of AST that inhibits 50% of infection intensity (the parasitemia rates (%)) compared to that of the AST-free control, was 13.9 µM. Thus, AST has activity against asexual blood stage forms.

Example 5—Transmission Blocking Activity of AST

Figure 4A:
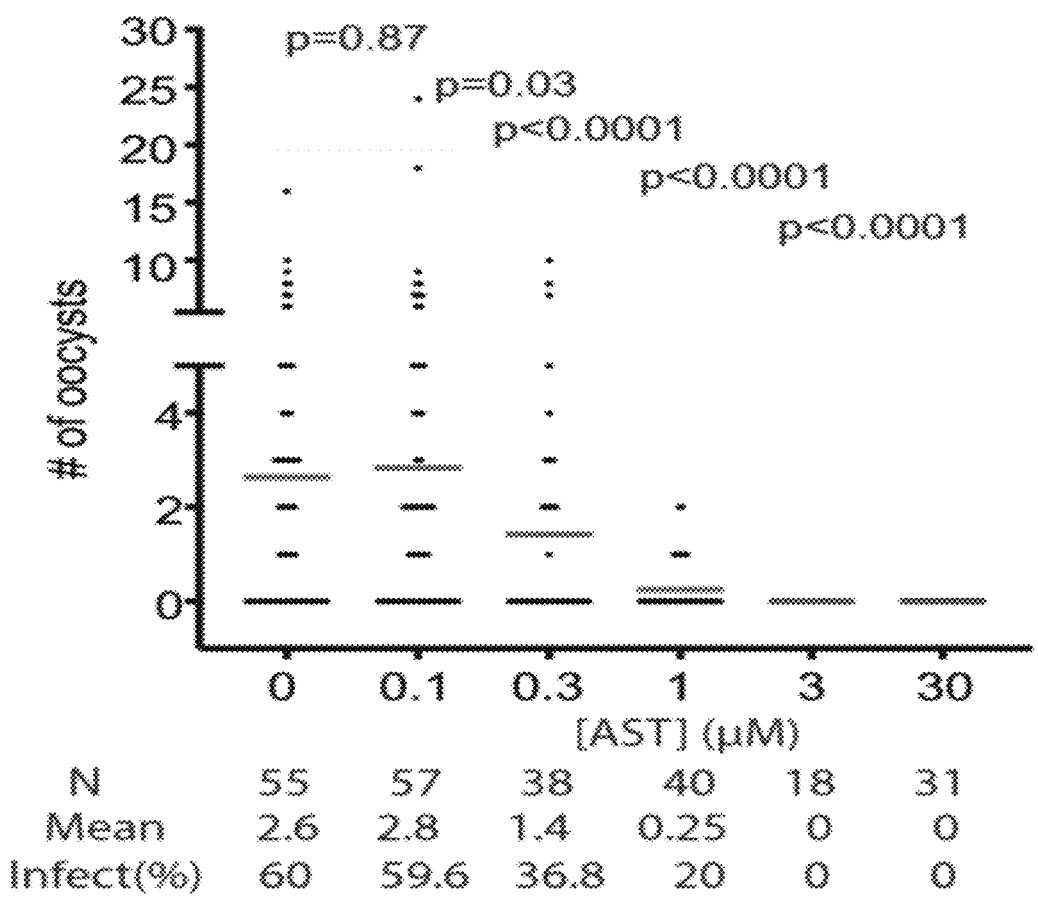
FIGS. 4A-4B show that AST blocks P. falciparum transmission to An. gambiae. (4A) The effects of AST on P. falciparum infection in Anopheles gambiae mosquitoes were analyzed using an SMFA as described in Materials and methods. Each dot on the chart represents a single midgut count. The mean oocyst number per midgut for each data set is indicated with a gray horizontal line. N=number of mosquitoes analyzed; Mean=mean oocyst number per midgut; Infect(%)=percentage of infected mosquitoes out of the total number of analyzed mosquitoes. Wilcoxon-Mann-Whitney test was used to calculate the p values. (4B) 15-day cultured P. falciparum-infected blood mixed with no drug (control) or 3 µM Arsinothricin (AST), phosphinothricin (PT) or methionine sulfoximine (MSO) was fed to An. gambiae using a standard membrane feeding assay (SMFA). The number of oocysts in mosquito midguts was counted on day 7 post-infection. Each dot on the chart represents a single midgut count. The mean oocyst number per midgut for each data set is indicated with a gray horizontal line.

The effects of AST on *P. falciparum* transmission to *Anopheles gambiae* mosquitoes was analyzed. AST was added to 15-day cultured *P. falciparum*-infected blood at concentrations from 0.1 to 3 µM and fed to *An. gambiae* using a standard membrane feeding assay (SMFA). The number of oocysts in mosquito midguts was counted on day 7 post-infection. AST completely inhibited malaria transmission at 3 µM (FIG. 4A) suggesting that AST effectively blocks transmission. Most of currently available antimalarial drugs and candidate drugs in clinical development require 5 µM or higher for complete inhibition of *P. falciparum* transmission in SMFAs. These results demonstrate that AST is at least as effective as current drugs. In contrast, no dead mosquitoes were observed, suggesting that AST has no or little insecticidal activity. The $EC_{50}$ of AST in blocking the transmission of the sexual-stage *P. falciparum* to mosquitos, defined as the concentration of a compound that inhibits 50% of infection intensity (the number of oocysts per mosquito) compared to that of the compound-free control, was 0.34 µM.

Figure 4B:
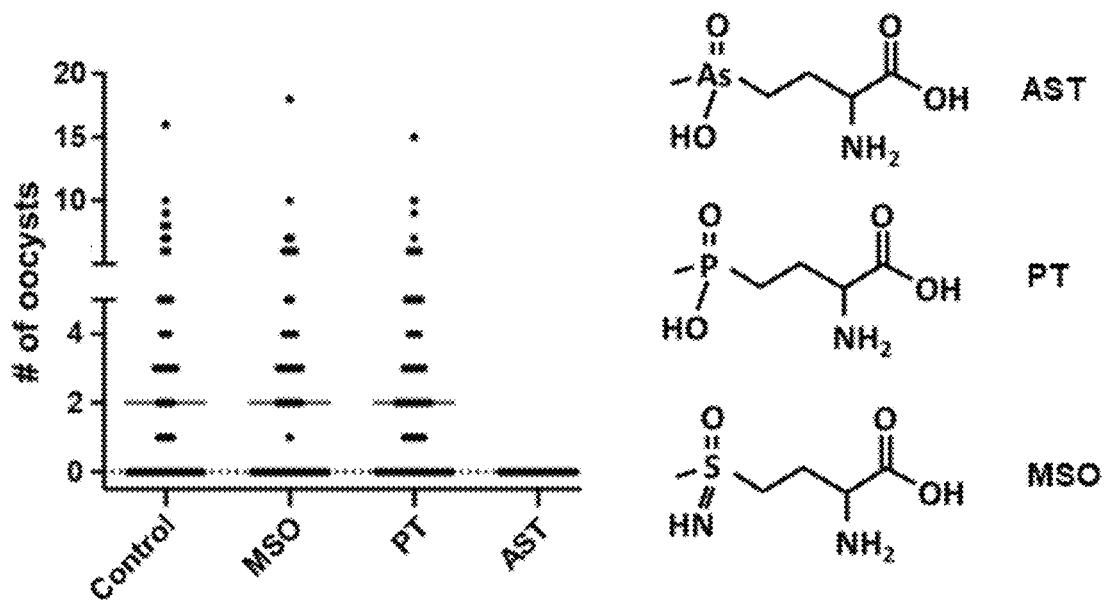

Advantageously, AST significantly inhibits *Plasmodium falciparum* transmission to *Anopheles gambiae* mosquitoes compared to that of PT and MSO (FIG. 4B).

Example 6—AST Shows Low Cytotoxicity to Human Cell Lines

Figures 5A, 5B:
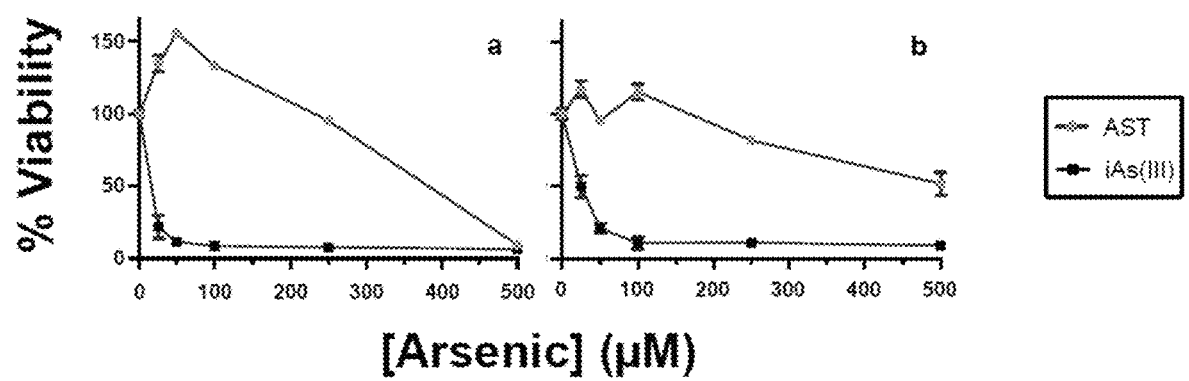
FIGS. 5A-5E show that AST is not toxic to human cells. Human cell lines, including, (5A) HEK293, immortalized embryonic kidney cells; (5B)THP-1, monocytes derived from an acute monocytic leukemia patient; (5C) macrophage, macrophage-like cells differentiated from THP-1; (5D) HepG2, immortalized cells isolated from a hepatocellular carcinoma; and (5E) Caco-2, immortalized cell line derived from a colorectal adenocarcinoma patient, were incubated in the presence or absence of the indicated concentrations of AST (gray circles) or As(III) (black squares) for 72 h, and viabilities were determined using MTT assays. Viabilities were normalized to the relative viability of untreated control samples (100%). AST cytotoxicity was evaluated and compared with that of As(III) using five different types of human cell lines. Data are presented using mean±SE (n=4).
Figures 5C, 5D:
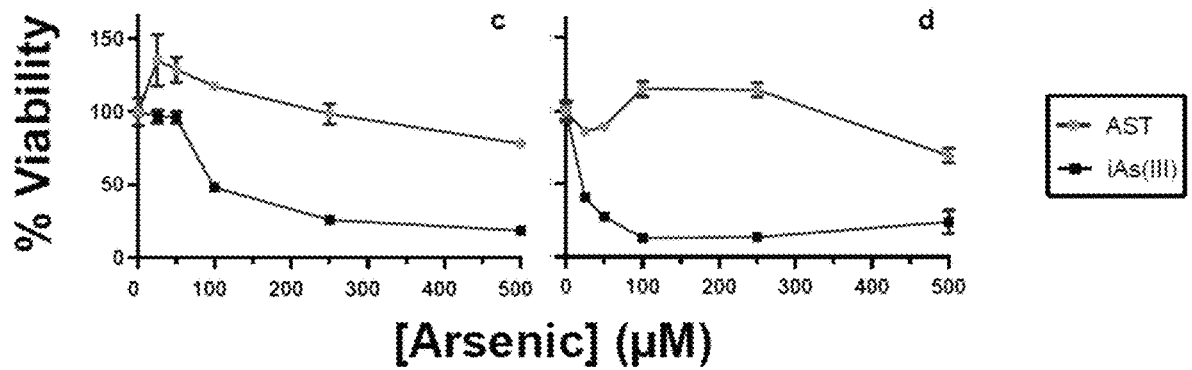
Figure 5E:
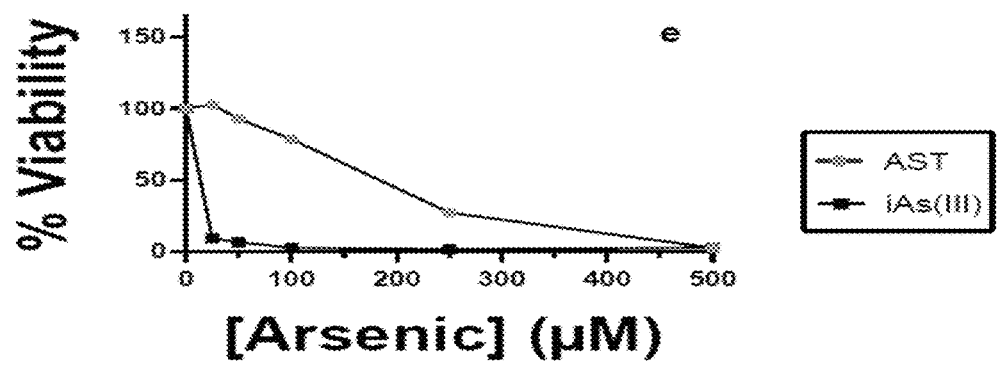

The AST cytotoxicity was evaluated and compared with that of inorganic As(III) using five different types of human cell lines from major organs/tissues: HEK293, immortalized embryonic kidney cells; THP-1, monocytes derived from an acute monocytic leukemia patient; macrophage, macrophage-like cells differentiated from THP-1; HepG2, immortalized cells isolated from a hepatocellular carcinoma; and Caco-2, immortalized cell line derived from a colorectal adenocarcinoma patient (FIG. 5). The results show that AST has much lower cytotoxicity in human cells than As(III). The $LC_{50}$ values of AST on all the tested cell lines except Caco2 were greater than 250 µM. Caco-2 was relatively more sensitive to AST with a lower $LC_{50}$ value (150-200 µM). In contrast, the $LC_{50}$ values of As(III) on all the tested cell lines except macrophage were lower than 25 µM, while that of macrophage was higher (100 µM), suggesting that AST is >10 times less cytotoxic than As(III). AST at 100 µM completely inhibits PfGS-I activity (FIG. 2C), *P. falciparum* proliferation in blood (FIG. 3) and transmission to mosquitoes (FIG. 4A), but had little effect on most of the tested human cell lines (FIG. 5). Thus, AST is effective against the malaria parasite with limited effect on human cells.

Example 7—AST Permeability and Stability in Human Cells

Figure 6:
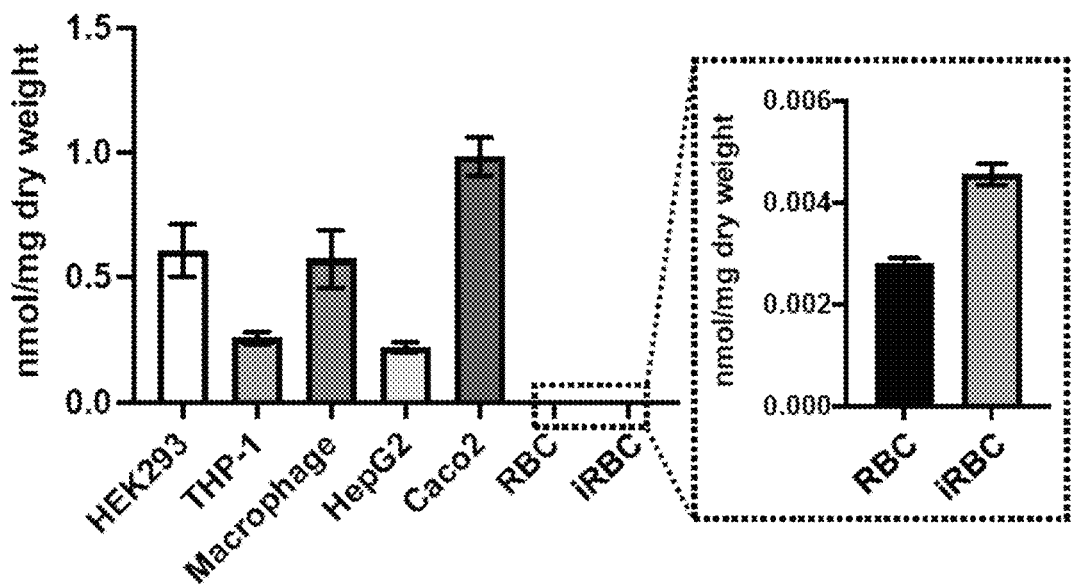
FIG. 6 shows permeability of AST to various human cell cytoplasmic membranes. Indicated human cell types were incubated with and without 100 µM AST for 48 h and total arsenic levels accumulated in cells were quantified by ICP-MS. Inset: The arsenic levels in RBC and iRBC are showing in the lower range (up to 6 µmol/mg dry weight). Values were obtained by subtracting control values (cells incubated without AST) from values of cells incubated with AST. Data are the mean±SE (n=3).

AST permeability and stability were investigated in cells of the five human cell lines. After incubation with AST at 100 µM for 2 days, total arsenic levels in cells (FIG. 6) and arsenic species in culture media (FIG. 7A) and cell lysates (FIG. 7B) were analyzed. Total arsenic levels increased inside all cell lines, yet the levels varied depending on the cell types, with the highest in Caco2 (FIG. 6). Arsenic species in both culture media (FIG. 7A) and cell lysates (FIG. 7B) were almost exclusively AST, demonstrating that AST is permeable to cytomembrane and stable in these tested human cell lines.

Figure 7A:
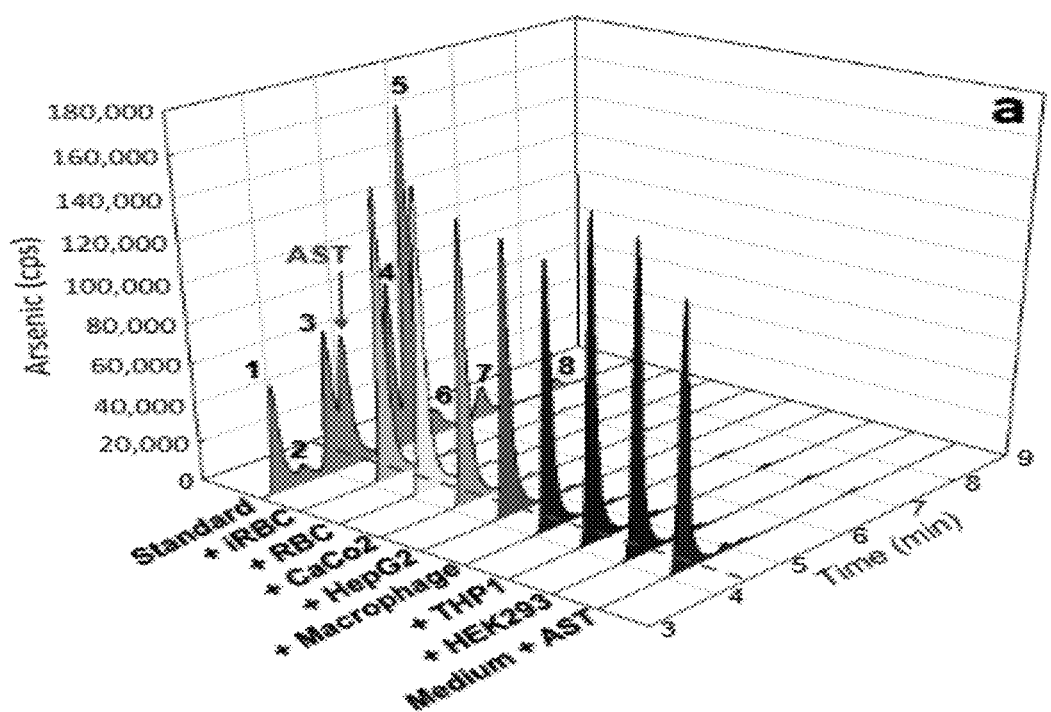
FIGS. 7A-7B show that AST is stable in culture media and human cell lines. Human cell lines were incubated with AST at 100 µM for 48 h. The arsenic species in culture media (7A) and cell lysates (7B) were analyzed by HPLC-ICP-MS. The data represent three replicates. Standard: 1, As(III); 2, MAs(III); 3, DMAs(V); 4, AST-OH; 5, Mas(V); 6, T-DMAs (V); 7, As(V); 8, T-MAs(V).
Figure 7B:
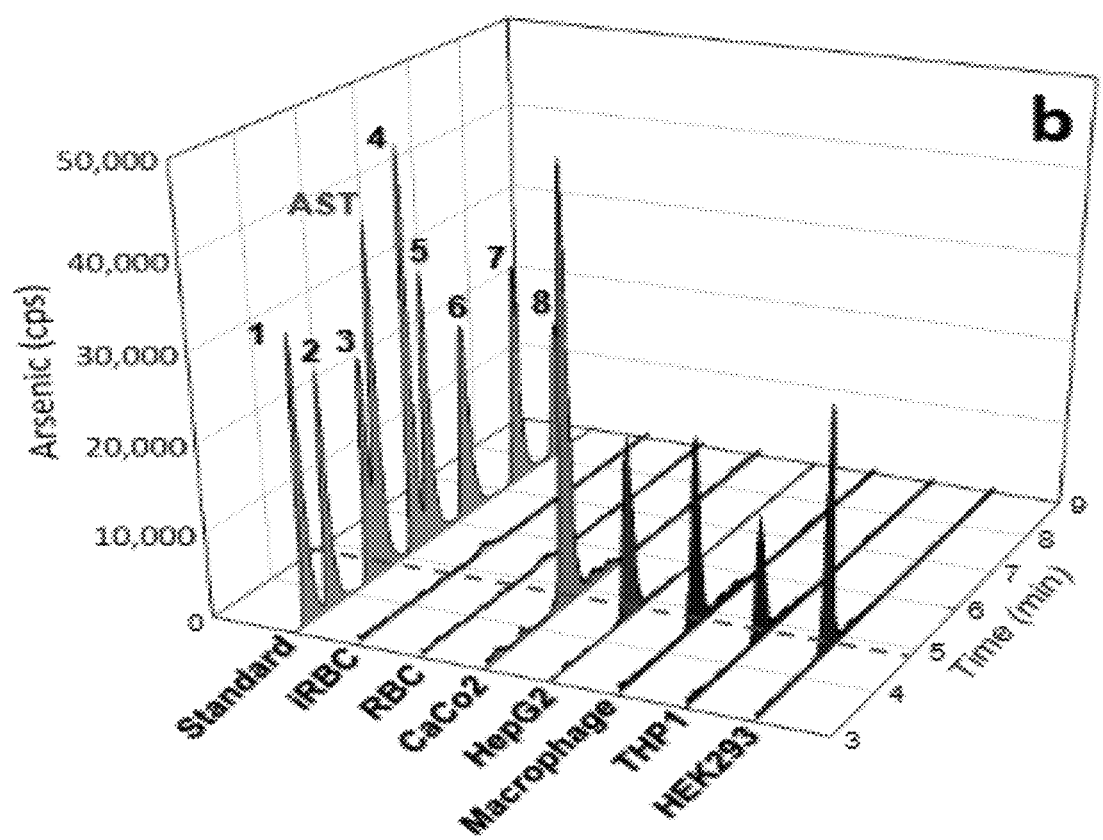

AST permeability and stability were examined in human erythrocytes (FIGS. 7A and 7B), which is relevant to the antimalarial activity of AST against asexual-stage parasites. Plasmodium parasites increase the permeability of the erythrocyte membrane to various low-molecular-weight solutes needed for growth by forming a new permeability pathway. The predominant arsenic species in the culture medium was almost exclusively AST, indicating that erythrocytes do not metabolize AST. Given AST's moderate anti-asexual activity (FIG. 3), it is anticipated that the erythrocyte membrane would be permeable to AST. Surprisingly, erythrocytes took up little AST regardless of malaria infection (FIGS. 7A and 7B). These results show that AST exerts its effect extracellularly, reducing parasitemia by attacking free merozoites released from schizonts rather than effecting parasites inside erythrocytes. Given that merozoite invasion of erythrocytes occurs within 5-10 min after rupture, AST can be effectively taken up by free merozoites, which in turn prevents erythrocyte invasion and/or proliferating, resulting in reduction of parasitemia in a concentration-dependent manner.

In summary, drug resistance is a significant factor in the increasingly difficult control of malaria. New drugs against new targets are urgently needed. Phylogenetically *Plasmodium* GS is more closely related to bacterial GS-I than to eukaryotic GS-II. Notably, the only active form of human GS (hGS-II), which is widely expressed in the major tissues/organs, belongs to GS-II. 1 µM of AST reduced the activity of PfGS-I by more than 60%, with little effect on hGS-II, demonstrating that AST highly selectively inhibits PfGS-I over hGS-II. GS-I, which consists of 12 identical subunits forming two hexameric rings, is evolutionarily and structurally distinct from GS-II, which consists of 10 subunits forming two pentameric rings. Despite the structural differences between the two forms, the residues involved in catalysis are highly conserved in PfGS-I and hGS-II (FIG. 8).

Figure 9A:
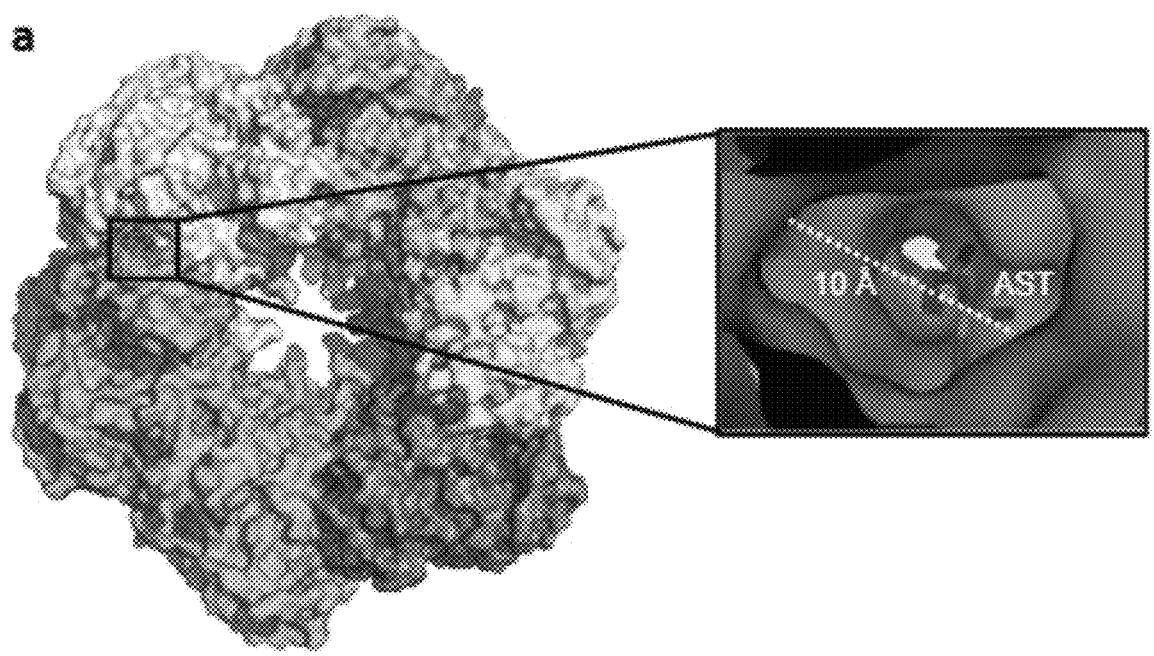
FIGS. 9A-9C show docking of AST with PfGS-I and hGS-II. (9A) Surface diagram of PfGS-I docked with AST. PfGS-I is a dodecamer composed of two hexameric rings with 12 active sites, each of which is formed between two monomers. AST molecule is docked with one of the glutamate-binding sites using AutoDock4. The approximate cavity width across the glutamate-binding site is 10 Å. (9B) Interaction of AST with PfGS-I. Residues predicted to be involved in AST-binding are shown in stick, where residues involved in binding of glutamate and ammonia are Arg356 and Asn297, and Glu362, respectively. The dotted lines represent hydrogen bonds. (9C) Surface diagram of hGS-II docked with AST. hGS-II is a decamer composed of two pentameric rings with 10 active sites, each of which is formed between two monomers. The AST molecule is docked with one of the glutamate-binding sites using AutoDock4. The approximate width of the cavity of the glutamate binding site is 6.5 Å.
Figure 9B:
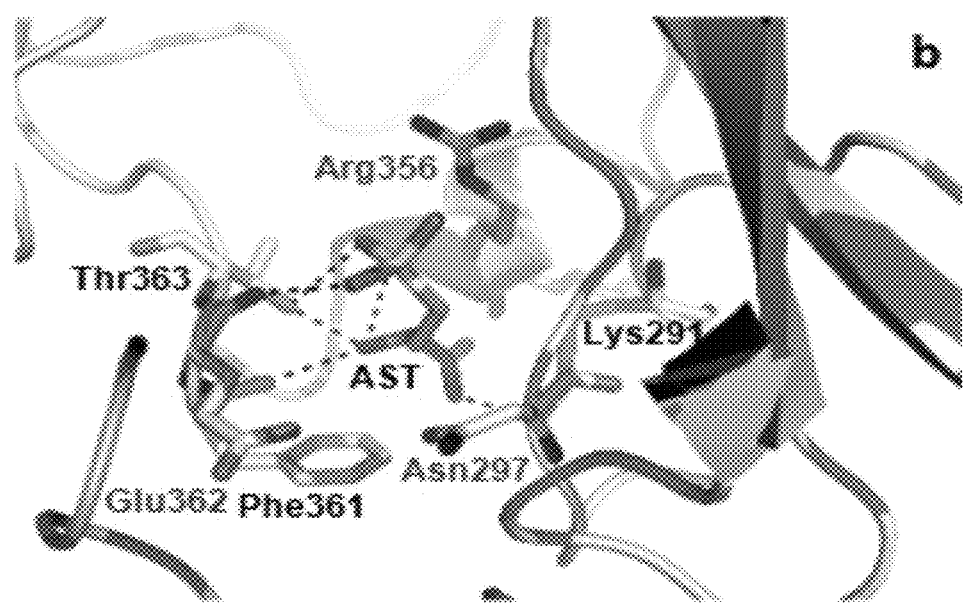
Figure 9C:
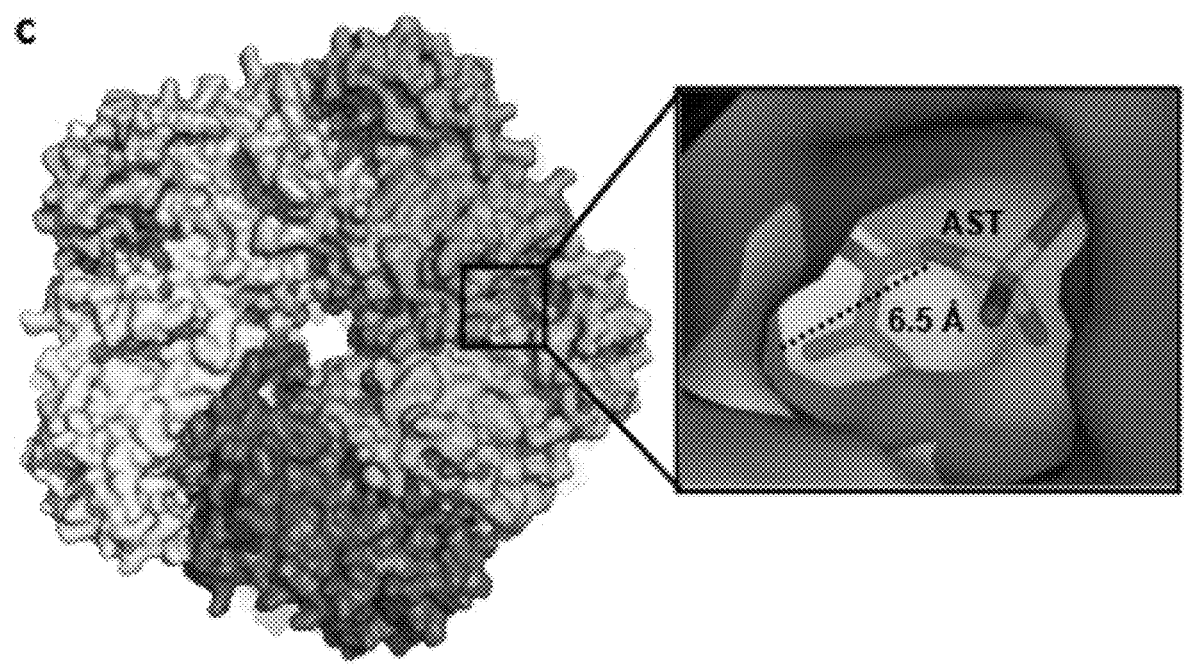

To shed light on the AST specificity, docking studies of AST on PfGS-I and hGS-II were conducted (FIGS. 9A-9C). The width of the active-site cavity of PfGS-I is approximately 10 Å, which allows the AST molecule to access the active site (FIG. 9A). AST molecule coordinates with six residues, including two glutamate-binding residues and one ammonia-binding residue (FIG. 9B), preventing the glutamate substrate from entering the active site. In contrast, the width of the active-site cavity in hGS-II is approximately 6.5 Å (FIG. 9C), much narrower than that of PfGS-I due to the close interaction of active site loops. The narrow cavity would limit the access of the AST molecule to the active site of hGS-II. Thus, the selectivity of AST for PfGS-I over hGS-II may be attributed to the difference in their active-site cavity size.

Given the poor permeability in erythrocytes, it is reasonable to consider that AST primarily targets free merozoites released from schizonts rather than parasites inside erythrocytes. The intraerythrocytic gametocytes, the sexual precursor cells of the malaria parasite, become activated in the mosquito midgut and subsequently egress from the enveloping erythrocytes for gamete formation and fertilization. As is the case with the asexual stage parasites, therefore, AST more likely actions after the parasite egress in the sexual stage. During the asexual stage, released merozoites rapidly invade fresh erythrocytes within 5-10 min after rupture to repeat the cycle, whereas the sexual stage gametocytes, after egressing from the enveloping erythrocytes, undergo two relatively longer processes of stage conversion, from gametocytes to gametes (~2 hours) and from zygotes to ookinetes (~18 hours), without the erythrocyte membrane barrier. The time difference of the exoerythrocytic period would be a major reason why higher concentration of AST may be required to control asexual stage parasites compared to the sexual stage parasites. In contrast to red blood cells, the other tested human cell lines are all permeable to AST. PfGS-I is expressed throughout all stages of the malaria parasite life cycle including sporozoites, the liver-infective forms. The results show that AST is moderately permeable to HepG2 cells, suggesting that AST can be a potent malaria prophylaxis.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. These examples should not be construed as limiting. In addition, any elements or limitations of any invention or embodiment thereof disclosed herein can be combined with any and/or all other elements or limitations (individually or in any combination) or any other invention or embodiment thereof disclosed herein, and all such combinations are contemplated within the scope of the invention without limitation thereto.

We claim:

1. A method of treating malaria infection in a subject in need thereof comprising administering to the subject arsinothricin (AST) or a salt thereof.

2. The method of claim 1, the malaria being caused by *P. falciparum, P. malariae, P. ovale, P. vivax, P. knowlesi, P. berghei, P. chabaudi* or *P. yoelii*.

3. The method of claim 1, the administration being via oral, pulmonary, buccal, suppository, intravenous, intraperitoneal, intranasal, intramuscular, or subcutaneous route.

4. The method of claim 1, the salt of AST being:
i) with an acid selected from hydrochloric acid, hydrobromic acid, perchloric acid, nitric acid, thiocyanic acid, sulfuric acid, phosphoric acid, trifluoroacetic acid (TFA), formic acid, acetic acid, propionic acid, lactic acid, pyruvic acid, oxalic acid, malonic acid, succinic acid, maleic acid, and fumaric acid, hexanoic acid, cyclopentanepropionic acid, glycolic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-di sulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid;
ii) with a base selected from sodium hydroxide, ammonium hydroxide, potassium hydroxide, monoalkyl amine, dialkyl amine, trialkyl amine, aryl amine, ammonium, and tetraalkylammonium; or
iii) with a metal selected from sodium, potassium, calcium, and magnesium.

5. The method of claim 1, the subject being a human.

6. The method of claim 1, the AST being L-AST.

7. The method of claim 1, the method further comprising detecting the activity of glutamine synthetase (GS) of the malaria parasite.

8. A method of inhibiting or reducing malaria transmission, the method comprising administering to a subject arsinothricin (AST) or a salt thereof.

9. The method of claim 8, the subject being a human having been infected by a malaria parasite.

10. The method of claim 9, the malaria parasite being *P. falciparum, P. malariae, P. ovale, P. vivax, P. knowlesi, P. berghei, P. chabaudi* or *P. yoelii*.

11. The method of claim 8, the administration being via oral, pulmonary, buccal, suppository, intravenous, intraperitoneal, intranasal, intramuscular, or subcutaneous route.

12. The method of claim 8, the AST being L-AST.

13. The method of claim 8, the salt of AST being:
i) with an acid selected from hydrochloric acid, hydrobromic acid, perchloric acid, nitric acid, thiocyanic acid, sulfuric acid, phosphoric acid, trifluoroacetic acid (TFA), formic acid, acetic acid, propionic acid, lactic acid, pyruvic acid, oxalic acid, malonic acid, succinic acid, maleic acid, and fumaric acid, hexanoic acid, cyclopentanepropionic acid, glycolic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-di sulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid;
ii) with a base selected from sodium hydroxide, ammonium hydroxide, potassium hydroxide, monoalkyl amine, dialkyl amine, trialkyl amine, aryl amine, ammonium, and tetraalkylammonium; or
iii) with a metal selected from sodium, potassium, calcium, and magnesium.

14. The method of claim 8, the method further comprising detecting the activity of GS of the malaria parasite.

15. A method of inhibiting or reducing the growth of malaria parasite in a subject having malaria, the method comprising administering to the subject AST or a salt thereof.

16. The method of claim 15, the subject being a human.

17. The method of claim 15, the malaria parasite being *P. falciparum, P. malariae, P. ovale, P. vivax, P. knowlesi, P. berghei, P. chabaudi* or *P. yoelii*.

18. The method of claim 15, the administration being via oral, pulmonary, buccal, suppository, intravenous, intraperitoneal, intranasal, intramuscular, or subcutaneous route.

19. The method of claim 15, the AST being L-AST.

20. The method of claim 15, the method further comprising detecting the activity of GS of the malaria parasite.

* * * * *

SEQUENCE LISTING

```
Sequence total quantity: 3
SEQ ID NO: 1            moltype = AA  length = 544
FEATURE                 Location/Qualifiers
source                  1..544
                        mol_type = protein
                        organism = Plasmodium falciparum
SEQUENCE: 1
MLIKLFFSNN AELYEYIKDK KNDVEIVACI ITNLLGTYFK CFFYVKEITL NKLESGFSFD   60
ASSIKLCSDT EVSDFFIKVD HSTCYLEECD GKNILNIMCD IKRYNGFDYY KCPRTILKKT  120
CEFVKNEGIA DKVCIGNELE FFIFDKVNYS LDEYNTYLKV YDRESFSCKN DLSSIYGNHV  180
VNKVEPHKDH FNNPNNEYLI NDDSKKVKKK SGYFTTDPYD TSNIIKLRIC RALNDMNINV  240
QRYHHEVSTS QHEISLKYFD ALTNADFLLI TKQIIKTTVS SFNRTATFMP KPLVNDNGNG  300
LHCNISLWKN NKNIFYHNDP STFFLSKESF YFMYGIVKHA KALQAFCNAT MNSYKRLVPG  360
FETCQKLFYS FGSRSAVIRL SLINYSNPSE KRIEFRLPDC ANSPHLVMAA IILAGYDGIK  420
SKEQPLVPFE SKDNHFYISS IFSKYVQHPE NFNILTHALE GYESLHTINE SPEFKNFFKC  480
EEPQGISFSL VESLDALEKD HAFLTVNNIF TEEMIQEYIK FKREEIDAYN KYVNAYDYHL  540
YYEC                                                               544

SEQ ID NO: 2            moltype = AA  length = 469
FEATURE                 Location/Qualifiers
source                  1..469
                        mol_type = protein
                        organism = Escherichia coli
SEQUENCE: 2
MSAEHVLTML NEHEVKFVDL RFTDTKGKEQ HVTIPAHQVN AEFFEEGKMF DGSSIGGWKG   60
INESDMVLMP DASTAVIDPF FADSTLIIRC DILEPGTLQG YDRDPRSIAK RAEDYLRSTG  120
IADTVLFGPE PEFFLFDDIR FGSSISGSHV AIDDIEGAWN SSTQYEGGNK GHRPAVKGGY  180
FPVPPVDSAQ DIRSEMCLVM EQMGLVVEAH HHEVATAGQN EVATRFNTMT KKADEIQIYK  240
YVVHNVAHRF GKTATFMPKP MFGDNGSGMH CHMSLSKNGV NLFAGDKYAG LSEQALYYIG  300
GVIKHAKAIN ALANPTTNSY KRLVPGYEAP VMLAYSARNR SASIRIPVVS SPKARRIEVR  360
FPDPAANPYL CFAALLMAGL DGIKNKIHPG EAMDKNLYDL PPEEAKEIPQ VAGSLEEALN  420
ELDLDREFLK AGGVFTDEAI DAYIALRREE DDRVRMTPHP VEFELYYSV              469
```

```
SEQ ID NO: 3           moltype = AA  length = 373
FEATURE                Location/Qualifiers
source                 1..373
                       mol_type = protein
                       organism = Homo sapiens
SEQUENCE: 3
MTTSASSHLN KGIKQVYMSL PQGEKVQAMY IWIDGTGEGL RCKTRTLDSE PKCVEELPEW   60
NFDGSSTLQS EGSNSDMYLV PAAMFRDPFR KDPNKLVLCE VFKYNRRPAE TNLRHTCKRI  120
MDMVSNQHPW FGMEQEYTLM GTDGHPFGWP SNGFPGPQGP YYCGVGADRA YGRDIVEAHY  180
RACLYAGVKI AGTNAEVMPA QWEFQIGPCE GISMGDHLWV ARFILHRVCE DPGVIATFDP  240
KPIPGNWNGA GCHTNFSTKA MREENGLKYI EEAIEKLSKR HQYHIRAYDP KGGLDNARRL  300
TGFHETSNIN DFSAGVANRS ASIRIPRTVG QEKKGYFEDR RPSANCDPFS VTEALIRTCL  360
LNETGDEPFQ YKN                                                    373
```